(12) United States Patent
Cao

(10) Patent No.: US 10,973,425 B2
(45) Date of Patent: Apr. 13, 2021

(54) HERMETICALLY SEALED IMPLANT SENSORS WITH VERTICAL STACKING ARCHITECTURE

(71) Applicant: INJECTSENSE, INC., Emeryville, CA (US)

(72) Inventor: Ariel Cao, Oakland, CA (US)

(73) Assignee: InjectSense, Inc., Emeryville, CA (US)

( * ) Notice: Subject to any disclaimer, the term of this patent is extended or adjusted under 35 U.S.C. 154(b) by 67 days.

(21) Appl. No.: 14/789,839

(22) Filed: Jul. 1, 2015

(65) Prior Publication Data

US 2016/0000344 A1 Jan. 7, 2016

Related U.S. Application Data

(60) Provisional application No. 62/019,841, filed on Jul. 1, 2014.

(51) Int. Cl.
*A61B 5/03* (2006.01)
*A61B 3/16* (2006.01)
(Continued)

(52) U.S. Cl.
CPC .............. *A61B 5/036* (2013.01); *A61B 3/16* (2013.01); *A61B 5/0215* (2013.01); *A61B 5/031* (2013.01);
(Continued)

(58) Field of Classification Search
CPC .......... A61B 2562/024; A61B 2562/12; A61B 2562/028; A61B 3/16; A61B 5/036;
(Continued)

(56) References Cited

U.S. PATENT DOCUMENTS 5,178,635 A 1/1993 Gwon et al.
5,466,233 A 11/1995 Weiner et al.
(Continued)

FOREIGN PATENT DOCUMENTS

CA 2904642 10/2014
CN 103190983 7/2013
(Continued)

OTHER PUBLICATIONS

Invitation to Pay Additional Fees and Partial Search Report dated Sep. 4, 2015, from International Application No. PCT/US2015/038917 (2 pages).
(Continued)

*Primary Examiner* — Devin B Henson
*Assistant Examiner* — H. Q. Nguyen
(74) *Attorney, Agent, or Firm* — Kilpatrick Townsend & Stockton LLP

(57) ABSTRACT

The present invention describes vertically stacked and hermetically sealed implantable pressure sensor devices for measuring a physiological signal. The implantable device comprises multiple layers, including a first wafer having a pressure sensor configured to measure the physiological signal and a second wafer having at least a digitizing integrated circuit. The first wafer is vertically stacked or disposed over the second wafer so as to form a hermetic seal. The device may include one or more additional layers adapted for energy storage and transfer, such as a third layer having a super-capacitor and a fourth layer having a thin film battery.

32 Claims, 20 Drawing Sheets

Cross-section B-B

(51) Int. Cl.
  *A61B 5/00* (2006.01)
  *A61B 5/0215* (2006.01)
  *A61B 5/07* (2006.01)
(52) U.S. Cl.
  CPC .............. *A61B 5/076* (2013.01); *A61B 5/686* (2013.01); *A61B 2560/0214* (2013.01); *A61B 2560/0475* (2013.01); *A61B 2562/0247* (2013.01); *A61B 2562/12* (2013.01)
(58) Field of Classification Search
  CPC ..... A61B 5/686; A61B 17/3468; A61B 5/076; A61F 9/0017; A61F 9/0026
  See application file for complete search history.

(56) References Cited

U.S. PATENT DOCUMENTS

| | | | |
|---|---|---|---|
| 5,626,559 | A | 5/1997 | Solomon et al. |
| 5,666,006 | A | 9/1997 | Townsley et al. |
| 5,868,697 | A | 2/1999 | Richter et al. |
| 6,186,974 | B1 | 2/2001 | Allan et al. |
| 6,193,656 | B1 | 2/2001 | Jeffries et al. |
| 6,346,742 | B1 | 2/2002 | Nasiri et al. |
| 6,666,841 | B2 | 12/2003 | Gharib et al. |
| 6,736,791 | B1 | 5/2004 | Bergheim et al. |
| 6,936,053 | B1 | 8/2005 | Weiss |
| 6,979,872 | B2 | 12/2005 | Borwick, III et al. |
| 6,981,958 | B1 | 1/2006 | Gharib et al. |
| 7,135,009 | B2 | 11/2006 | Tu et al. |
| 7,149,587 | B2 | 12/2006 | Wardle et al. |
| 7,163,543 | B2 | 1/2007 | Smedley et al. |
| 7,186,232 | B1 | 3/2007 | Smedley et al. |
| 7,431,710 | B2 | 10/2008 | Niksch et al. |
| 7,488,303 | B1 | 2/2009 | Haffner et al. |
| 7,509,169 | B2 | 3/2009 | Eigler et al. |
| 7,563,241 | B2 | 7/2009 | Tu et al. |
| 7,678,065 | B2 | 3/2010 | Haffner et al. |
| 7,708,711 | B2 | 5/2010 | Gharib et al. |
| 7,732,302 | B2 | 6/2010 | Yazdi |
| 7,819,014 | B1 | 10/2010 | Broden |
| 7,850,637 | B2 | 12/2010 | Lynch et al. |
| 7,867,186 | B2 | 1/2011 | Smedley et al. |
| 7,900,518 | B2 | 3/2011 | Tai et al. |
| 7,951,155 | B2 | 5/2011 | Burns et al. |
| 8,118,768 | B2 | 2/2012 | Tu et al. |
| 8,142,364 | B2 | 3/2012 | Haffner et al. |
| 8,303,511 | B2 | 11/2012 | Whiting et al. |
| 8,322,346 | B2 | 12/2012 | Najafi et al. |
| 8,336,387 | B2 | 12/2012 | Tai et al. |
| 8,337,445 | B2 | 12/2012 | Niksch et al. |
| 8,475,374 | B2 | 7/2013 | Irazoqui et al. |
| 8,478,415 | B1 | 7/2013 | Halla et al. |
| 8,506,515 | B2 | 8/2013 | Burns et al. |
| 8,549,925 | B2 | 10/2013 | Tai et al. |
| 8,585,630 | B2 | 11/2013 | Meng et al. |
| 8,808,181 | B2* | 8/2014 | Jain .................... A61B 5/0017 257/431 |
| 9,022,968 | B2 | 5/2015 | Passaglia |
| 9,111,473 | B1 | 8/2015 | Ho et al. |
| 9,173,564 | B2 | 11/2015 | Choo et al. |
| 9,301,875 | B2 | 4/2016 | Tu et al. |
| 9,314,375 | B1 | 4/2016 | Passaglia |
| 9,398,868 | B1 | 7/2016 | Otis et al. |
| 10,213,107 | B2 | 2/2019 | Cao et al. |
| 2002/0115920 | A1 | 8/2002 | Rich et al. |
| 2003/0060752 | A1 | 3/2003 | Bergheim et al. |
| 2003/0060763 | A1* | 3/2003 | Penfold ................ A61F 9/0017 604/116 |
| 2003/0078487 | A1 | 4/2003 | Jeffries et al. |
| 2004/0050392 | A1 | 3/2004 | Tu et al. |
| 2004/0073137 | A1 | 4/2004 | Lloyd et al. |
| 2004/0104754 | A1 | 6/2004 | Bruchhaus et al. |
| 2004/0116524 | A1 | 6/2004 | Cohen et al. |
| 2004/0215133 | A1 | 10/2004 | Weber et al. |
| 2005/0019371 | A1 | 1/2005 | Anderson et al. |
| 2005/0196424 | A1 | 9/2005 | Chappa |
| 2005/0288604 | A1 | 12/2005 | Eigler et al. |
| 2005/0288722 | A1 | 12/2005 | Eigler et al. |
| 2006/0106434 | A1 | 5/2006 | Padgitt et al. |
| 2006/0247539 | A1 | 11/2006 | Schugt et al. |
| 2007/0156079 | A1 | 7/2007 | Brown et al. |
| 2008/0057106 | A1 | 3/2008 | Erickson et al. |
| 2008/0097335 | A1 | 4/2008 | Trogden et al. |
| 2008/0161741 | A1 | 7/2008 | Bene et al. |
| 2009/0196903 | A1 | 8/2009 | Kliman |
| 2010/0016704 | A1 | 1/2010 | Naber et al. |
| 2010/0152646 | A1 | 6/2010 | Girijavallabhan et al. |
| 2010/0280349 | A1 | 11/2010 | Dacquay et al. |
| 2011/0082385 | A1 | 4/2011 | Diaz et al. |
| 2011/0298465 | A1* | 12/2011 | Yuasa ................ H01L 21/67253 324/464 |
| 2011/0301434 | A1 | 12/2011 | Haque et al. |
| 2011/0309458 | A1* | 12/2011 | Gamage ................ G01L 9/0042 257/419 |
| 2012/0004528 | A1 | 1/2012 | Li et al. |
| 2012/0078362 | A1 | 3/2012 | Haffner et al. |
| 2012/0165933 | A1 | 6/2012 | Haffner et al. |
| 2012/0197101 | A1 | 8/2012 | Telandro |
| 2012/0197155 | A1* | 8/2012 | Mattes ................ A61B 5/0215 600/561 |
| 2012/0200408 | A1 | 8/2012 | Gotschlich et al. |
| 2012/0209100 | A1* | 8/2012 | De Beeck ........... H01L 23/3114 600/377 |
| 2012/0226132 | A1 | 9/2012 | Wong et al. |
| 2012/0226133 | A1 | 9/2012 | Wong et al. |
| 2012/0253258 | A1 | 10/2012 | Tu et al. |
| 2012/0259195 | A1 | 10/2012 | Haffner et al. |
| 2012/0302861 | A1 | 11/2012 | Marshall et al. |
| 2013/0001550 | A1* | 1/2013 | Seeger .................... G01L 5/223 257/48 |
| 2013/0009053 | A1 | 1/2013 | Wu |
| 2013/0018440 | A1 | 1/2013 | Chow et al. |
| 2013/0036827 | A1 | 2/2013 | Besling |
| 2013/0046166 | A1 | 2/2013 | Maleki Jafarabadi et al. |
| 2013/0085440 | A1 | 4/2013 | Bohm et al. |
| 2013/0090534 | A1 | 4/2013 | Burns et al. |
| 2013/0184554 | A1 | 7/2013 | Elsheikh et al. |
| 2013/0253528 | A1* | 9/2013 | Haffner ................ A61F 9/0017 606/107 |
| 2013/0298699 | A1 | 11/2013 | Potasek |
| 2013/0324942 | A1 | 12/2013 | de Juan, Jr. et al. |
| 2014/0012177 | A1 | 1/2014 | Tu et al. |
| 2014/0016097 | A1 | 1/2014 | Leonardi et al. |
| 2014/0039456 | A1 | 2/2014 | Lerner |
| 2014/0088400 | A1 | 3/2014 | Irazoqui et al. |
| 2014/0268524 | A1* | 9/2014 | Gogoi ..................... H01L 27/14 361/679.01 |
| 2014/0275923 | A1 | 9/2014 | Haffner et al. |
| 2014/0303544 | A1 | 10/2014 | Haffner et al. |
| 2016/0000325 | A1 | 1/2016 | Cao et al. |
| 2016/0015265 | A1 | 1/2016 | Mandel et al. |
| 2016/0015266 | A1 | 1/2016 | Kim et al. |
| 2016/0064867 | A1 | 3/2016 | Bergner |
| 2017/0251921 | A1 | 9/2017 | Truong et al. |

FOREIGN PATENT DOCUMENTS

| | | |
|---|---|---|
| JP | 2013017573 | 1/2013 |
| JP | 2013505078 | 2/2013 |
| WO | 2009129450 | 10/2009 |
| WO | 2011035262 | 3/2011 |
| WO | 2013003789 | 1/2013 |
| WO | 2013040079 | 3/2013 |
| WO | 2013056130 | 4/2013 |

OTHER PUBLICATIONS

Invitation to Pay Additional Fees and Partial Search Report dated Sep. 10, 2015, from International Application No. PCT/US2015/038862 (2 pages).

Haque, R.M. et al., "A 3D Implantable Microsystem for Intraocular Pressure Monitoring Using a Glass-In-Silicon Reflow Process,"

(56) References Cited

OTHER PUBLICATIONS

Micro Electro Mechanical Systems (MEMS), Jan. 23-27, 2011, IEEE 24th International Conference, pp. 995-998.
Haque, R.M. et al., "Hermetic Packaging of Resonators With Vertical Feedthroughs Using a Glass-In-Silicon Reflow Process," Solid-State Sensors, Actuators and Microsystems 16th International IEEE Conference, Transducers, Jun. 5-9, 2011, pp. 2303-2306.
Wang, Fei et al., "Electrostatic Energy Harvesting Device With Out-Of-The-Plane Gap Closing Scheme," Sensors and Actuators A: Physical, Jan. 2014, 4 pages.
International Search Report and Written Opinion dated Oct. 6, 2015, from International Application No. PCT/US2015/038902 (12 pages).
"Auto Regulation System for Intraocular Pressure", USF Available Technologies, Technology Transfer Office http://www.usf.edu/research-innovation/pl/, 1 page.
"MEMS Intraocular Pressure Sensor", SBIR.gov, https://www.sbir.gov/sbirsearch/detail/214217, 2 pages.
"Nanophotonics-Based Implantable Iop-Sensor With Remote Optical Readout", https://techtransfer.universityofcalifornia.edu/NCD/24177.html, 5 pages.
"Optical-Based Intraocular Pressure Sensor", Research Affairs, Office of Innovation and Commercialization, US San Diego, https://techtransfer.universityofcalifornia.edu/NCD/24855.html, 5 pages.
"The Choo Lab", Division of Engineering and Applied Science, httpiieas.caltech.edu, http:/ I choo lab. caltech. edu/research.html, 4 pages.
AcuMEMS Inc. , "AcuMEMS Announces New Glaucoma Product for Cataract Surgery", AcuMEMS Announces New Glaucoma Product for Cataract Surgery , Business Wire. http://www.businesswire.com/news/home/20101015005202/en/AcuMEMS-Announces-New-Glaucoma-Product-Cataract-Surgery, Oct. 15, 2010, 2 pages.
Araci et al., "An implantable microfluidic device for selfmonitoring of intraocular pressure", Nature Medicine 20, 2014, pp. 1074-1078.
Bhamra, "Implantable Ultra-Miniature IntraOcular Pressure Sensor", CID Home, Implantable Ultra-Miniature Intra-Ocular Pressure Sensor—Center for Implantable Devices, https :/I engineering. purdue. edu/CID /implantable-ocular-pressure-sensor .html, 2 pages.
Caceres , "Nanophotonics-based implant may enable at-home IOP monitoring", OphthalmologyTimesOphthalmologvCalit{ )rnia Institute of Technology, http://ophthalmologytimes.modernmedicine.com/ ophthalmologytimes/content/tags/california, Jul. 15, 2014, 3 pages.
Goldberg et al., "Glaucoma Forum Shedding Light on 'Silent Thief of Sight'", Glaucoma Research Foundation, https://www.glaucoma.org/research/glaucoma-forum-shedding-light-on-silent-thief-of-sight, Feb. 11, 2014, 4 pages.
Kim et al., "Performance of implantable inductive pressure sensor for continuous monitoring of intraocular pressure", ARVO Annual Meeting Abstract, Investigative Ophthalmology & Visual Science vol. 55, 121. doi:http://iovs. arvoj ournals. org/ article.aspx?articleid= 22664 3 7, Apr. 2014, 3 pages.
Kim et al., "Preliminary study on implantable inductive-type sensor for continuous monitoring of intraocular pressure", Clinical & Experirnenta! Ophthalmology, vol. 43, Issue 9, Dec. 2015, pp. 830-837.
Launch Point Technologies Inc. , "Intraocular Pressure Sensor: LaunchPoint Technologies", Launch Point Technologies, http://www.launchpnt.com/portfolio/biornedical/intraocular-pressure-sensor, 3 pages.
Lee et al., "Nanoarray-Enhanced Micro mechanical Pressure Sensor with Remote Optical Readout", Advanced Photonics, paper SeTh2D. 3, 2014, 2 pages.
Lin et al., "High Quality Factor Parylene-Based Intraocular Pressure Sensor", 2012 7th IEEE International Conference on Nano/Micro Engineered and Molecular Systems (NEMS), 2012, pp. 137-140.
Liu et al., "Estimation of 2~-Hour Intraocular Pressure Peak Timing and Variation Using a Contact Lens Sensor", PLoS One. vol. 10(6), e0129529, Jun. 15, 2015, pp. 1-11.
Ma , "Sensor in eye could track pressure changes, monitor for glaucoma", UW News, Engineering, Health and Medicine, New Releases, Research, Science, Technology http :I !www. washington. edu/news/20 14/06/16/sensor-in-eye-could-track-pressure-changes-monitor-for-glaucoma, Jun. 16, 2014, 5 pages.
Quake , "Eye implant could lead to better glaucoma treatment", News Center, Stanford Medicine http://med.stanford.edu/news/all-news/20 14/08/eye-implant-could-lead-to-better-glaucoma-treatment, Aug. 25, 2014, 3 pages.
Thieme , "New chances for glau om a patients", glaucoma treatment—EYEMATE, Your intraocular pressure look-out, http://www.my-eyemate.com/en/, 4 pages.

* cited by examiner

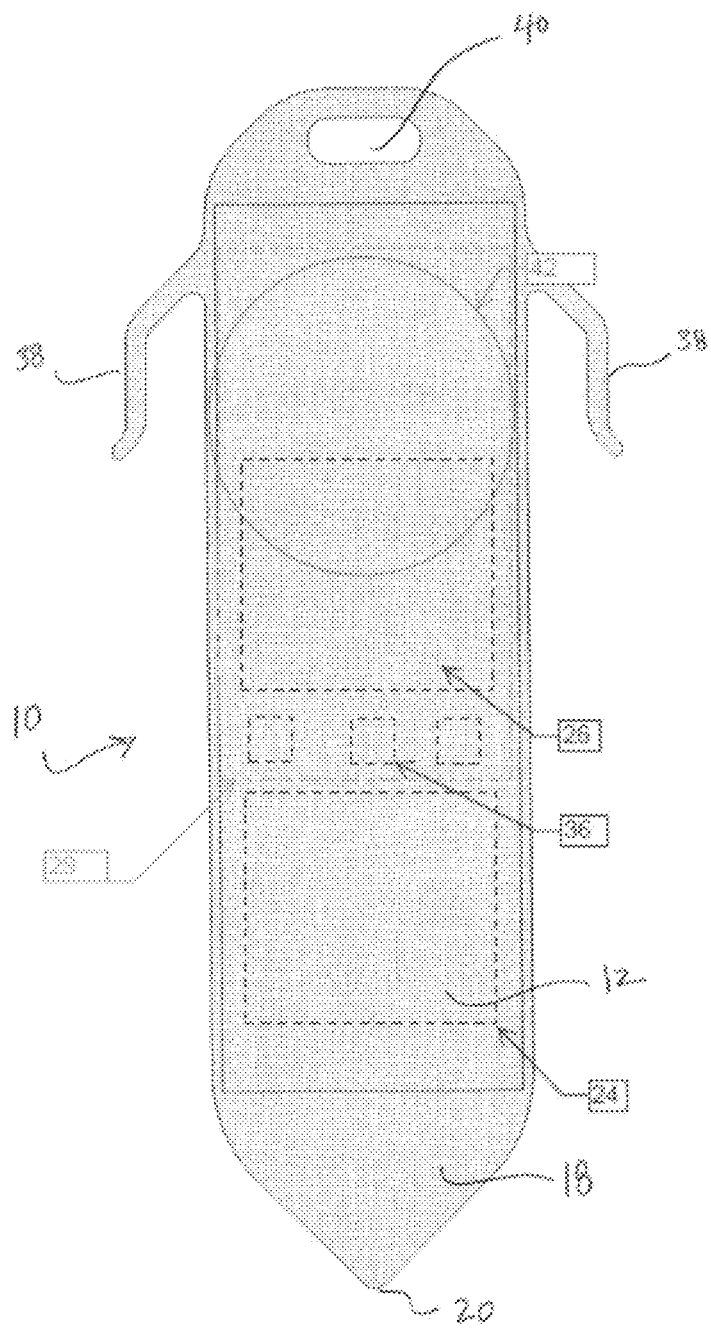
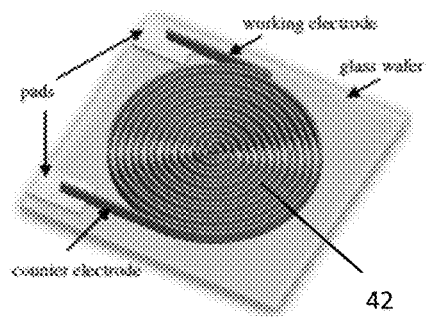
FIG. 4D
FIG. 4E

Cross-section A-A

Cross-section B-B

FABRICATION PROCESS

1) Fabricate Sensor

2) Bond ASIC to Sensor

3) Bond Battery to ASIC + Sensor

4) Mount Stack in Package

5) Finished Assembly

HERMETICALLY SEALED IMPLANT SENSORS WITH VERTICAL STACKING ARCHITECTURE

CROSS-REFERENCES TO RELATED APPLICATIONS

The present application is a Non-Provisional of and claims the benefit of priority of U.S. Provisional Application No. 62/019,841 filed on Jul. 1, 2014, the entire of contents of which are incorporated herein by reference.

The present application is related to co-assigned and concurrently filed U.S. Non-Provisional patent application Ser. No. 14/789,491 (now U.S. Pat. No. 10,213,107) and U.S. Non-Provisional patent application Ser. No. 14/789,942; each of which is incorporated herein by reference in its entirety for all purposes.

BACKGROUND OF THE INVENTION

Glaucoma is associated with elevated levels of intraocular pressure (IOP) and can permanently damage vision in the affected eye(s) and lead to irreversible blindness if left untreated. Glaucoma is due to damage of the optic nerve due to increased fluid pressure in the eye. Currently, about 60 million people worldwide suffer from glaucoma, with that estimate expected to rise to about 80 million people in 2020. In the United States alone, there are about 2.2 million patients with glaucoma resulting in approximately 10 million physician visits each year and health care costs of about 1.5 billion dollars annually.

In many instances, glaucoma related vision impairments can be prevented if diagnosed and treated in the early stages of disease progression or even before the onset of glaucoma (i.e., pre-glaucoma patients). Because glaucoma is usually associated with an increase in IOP, primary open angle glaucoma and normal tension glaucoma being dominant variations of the disease, periodic testing can be used to monitor glaucoma in order to prevent vision loss. Conventional standard of care requires a patient to visit an eye clinic four to six times a year for non-invasive measurement of the patient's IOP, such as tonometry. While tonometry techniques are generally low cost, easy, and non-invasive, a number of different types of errors can significantly reduce the accuracy of this diagnostic tool and as such potentially result in inappropriate diagnosis and/or ineffective follow-up medical treatment.

For example, at least some of these non-invasive clinical techniques may not detect elevated IOP levels (e.g., pressure spikes) as only a single point measurement is taken during an eye exam. Failure to continuously and/or frequently monitor IOP levels outside the eye clinic (e.g., more than four to six measurements per year) may lead to inaccurate detection of the patient's real IOP profile (e.g., real IOP may be higher or lower than measured IOP). Non-invasive measurements in some instances also lack accuracy as these devices measure pressure of the eye with an external sensor that provides an indirect measurement of the actual pressure inside the eye. For example, factors that affect accuracy may include failure to account for anatomical differences, such as a patient's cornea thickness, scleral rigidity, or conical curvature, variances due to operator's use or technique, physiological influences, such as as caffeine or alcohol use, or prior refractive surgery that may affect a patient's IOP, etc. Hence, the indirect IOP measurements from such non-invasive devices may differ from the actual IOP inside the eye (e.g., overestimated or underestimated) which may lead to inappropriate diagnosis and/or follow-up treatment. Further, it often inconvenient and unpractical for patients to visit the eye clinic on a strict regular schedule for IOP measurement.

Although implantable IOP devices have been proposed for direct IOP measurements on a daily basis, these first generation implants may also suffer from several drawbacks which in turn may result in indirect and/or inaccurate measurement of IOP and inappropriate medical treatment of glaucoma. For example, the IOP devices may be too large or bulky in dimension, size or shape to be safely and effectively placed entirely within a desired location or structure of the eye for direct measurement of IOP. Further, some devices may be extremely invasive, requiring major surgery for implantation and/or complicated positioning of multiple components which are each implanted in different structures or areas of the eye, which unnecessarily increases patient risk and/or injury and total healthcare costs.

Further, some IOP implantable devices may utilize pressure ports which are susceptible to sensing inaccuracies or require direct implantation within certain anatomical locations, such as the anterior chamber, posterior chamber, suprachoroidal space, or cornea of the eye which may lead to unanticipated complications. Also, some of these devices may not be well suited for chronic implantation due to IOP implant design issues of water ingress and/or thermal stress (e.g., associated with polymer packaging), which in turn precludes continuous monitoring of IOP. Such proposed flexible sensors also have issued of degraded stability. In some instances, some IOP devices also suffer from poor calibration and/or monitoring is not adjustable so as to further result in inaccurate IOP detection levels.

Accordingly, it would be desirable to provide improved implant devices and methods of implantation that overcome at least some the above mentioned shortcomings. In particular, it would be desirable to develop ultra-miniature implantable IOP devices that accurately, continuously, and adjustably monitor IOP levels. Ideally, such devices should directly measure IOP pressure levels and can be safely and effectively implanted entirely within a desired location within the eye quickly and easily in an outpatient environment, such as the physician's office, without invasive major surgery. Further, such devices should allow for chronic implantation so as to provide long-term stable and continuous IOP measurement profiles for appropriate diagnosis and follow-up therapy.

BRIEF SUMMARY OF THE INVENTION

Embodiments of the present invention provide improved micro-electrical mechanical system (MEMS) based pressure sensor implants for the accurate measurement of physiological signals, such as IOP, on a continuous or frequent basis for appropriate treatment of glaucoma. A particular advantage of the present invention is the implant architecture design and construction which allows the implant form factor (e.g., dimension, size, shape, volume, etc.) to be significantly reduced. This ultra-miniature form factor is important for several reasons.

For example, the ultra-miniature form factor allows for implantation of the MEMS implant through an injector, syringe, or like delivery systems having a gauge of 19 (e.g., inner diameter of approximately 690 microns) or higher (e.g., up to 28 or 29 gauge). This in turn enables a relatively quick, easy, and safe implantation procedure in an outpatient environment (e.g., 5-10 minutes of surgical time), such as the physician's office, without major invasive surgery which likely results in significant savings to the health system and reduced patient complications. Further, the reduced invasiveness of an injectable pressure sensor implant allows for diagnosis of not only glaucoma patients, but also pre-glaucoma patients. Early diagnosis and follow-up medical therapy could prevent complicated glaucoma surgery (e.g., laser surgery, trabeculectomy, valve implants), vision impairments, and/or blindness in the later years. As most ophthalmologist are well trained in injectables for drug therapies, such as injection of anti-VEGF drugs associated with treatment of age related macular degeneration, adoption of injectable pressure sensor implants should also be relatively well accepted.

Another benefit of the ultra-miniature form factor is that it allows the MEMS implant to be safely and effectively implanted entirely within a desired location within the eye so as to directly measure IOP levels. Accurate IOP profiles are beneficial for guiding appropriate, safe, and effective therapies for glaucoma control and management, which may include therapeutic pharmaceuticals, implantable shunt or drainage devices, glaucoma surgery, and/or the like. Such implantable IOP pressure sensors further monitor patients for continued compliance with the prescribed treatments, which can be particularly of benefit in medically controlled IOP patients.

It will be appreciated, however, that the implant devices of the present invention are not limited to solely the ophthalmology space and the diagnosis and treatment of glaucoma, but may find beneficial application in several other medical fields where it is desirable to have an ultra-miniature, injectable implant that provides diagnostic transducer measurements accurately, adjustably, and continuously. For example, such other physiological applications include but are not limited to sensing of an intracranial pressure, a cardiovascular pressure at a location such as the pulmonary artery, and monitoring of glucose, urology parameters such as abdominal compartment syndrome diagnosed with bladder pressure, eye motion controlled or uncontrolled with conditions like horizontal, vertical or torsional nystagmus, or acute compartment syndrome when a patient is under severe trauma condition such broken leg which is causing excessive pressure builds up inside an enclosed space (measured in terms of strain) within the muscle tissue such as arms, legs. At least some of these physiological sensors may utilize one or more additional sensors on the implantable sensor device.

In many embodiments of the present invention, vertically stacked and hermetically sealed implantable pressure sensor devices for measuring a physiological signal of a patient or animal are described. The implantable device comprises a first wafer and a second wafer. The first wafer comprises at least a pressure sensor configured to measure the physiological signal. The second wafer comprises at least a digitizing integrated circuit. The first wafer is vertically stacked or disposed over the second wafer so as to form a hermetic seal. In particular, the vertical stacking of the wafers is configured to create a hermetically sealed cavity between the first and second wafers.

This vertical stacking architecture design and construction, which is described in greater detail below, allows for the implant to define its own hermetic package and significantly reduce its form factor so as to be easily implanted as an injectable and within a desired location within the eye. In particular, the implantable device may comprise a size or shape capable of implantation through an injector or syringe having a gauge of 19 or higher. The implantable device may also be sized or shaped to be positionable within a vitreous body of an eye so as to measure an IOP of a vitreous humour which provides a safe region within the physiology of the eye. Other locations such as the anterior chamber where the aqueous humour accumulated can be also directly monitored but at a greater risk to impair the vision of the patient. Monitoring the anterior chambers directly is not worth the risk of affecting vision significantly or the associated liability. Even if there were a slight degradation or attenuation in IOP when measuring within the vitreous humour, the increased pressure may be detected with a continuous pressure profile that will satisfactorily quantify the increase in pressure. The proposed measurement locations can be readily validated across a range of animal models, which may also be used to adjust the sensor sensitivity if necessary.

The pressure sensor of the implantable device may comprise a capacitive pressure transducer. In some embodiments, the device includes an absolute reference with a vacuum within the transducer and may include a differential mode using two capacitors for sensing and reference, respectively. It will be appreciated however that the first wafer may incorporate other types of sensors or transducers, such as an accelerometer or piezoelectric, depending on the desired physiological signal for measurement and sensing. The capacitive pressure transducer comprises at least a first cavity structure and a second cavity structure, wherein the at least first cavity is distal of the at least second cavity. The at least first cavity is under vacuum so as measure the physiological signal, such as IOP, while the at least a second cavity structure is configured to measure a reference pressure of one more parameters other than the IOP so that it is independent of the actual IOP measured by the at least first cavity. The second cavity has also vacuum but the membrane has a reduced area to significantly reduce the sensitivity to pressure but with the same electrical characteristic (e.g. capacitance).

The second wafer further comprises a radio frequency link, power storage, and data storage. Alternatively, such elements may be incorporated into a third wafer comprising at least a second digitizing integrated circuit, wherein the second wafer is vertically stacked or disposed over the third wafer. Each wafer comprises a maximum thickness of about 200 microns or less, and more particularly a maximum thickness of about 125 microns or less. In some examples, the first wafer has a greater thickness than the second wafer so as provide for sufficient rigidity of the pressure sensor, while in other examples each wafer can have substantially the same thickness. The implantable device may comprise a maximum thickness of about 650 microns or less, a maximum length of about 4 mm or less, and a width of 650 microns or less, and more particularly a maximum thickness of about 600 microns or less, a maximum length of about 3 mm or less, and a width of 600 microns or less. In some embodiments, the device dimensions are about 520 um in width and 450 um in thickness, which can be reduced by at least 20% for smaller gauge syringe. In one aspect, the sensor device is dimensioned so as to be inserted through the sclera, which at the pars plana is about 0.5 m thick+/−0.2 mm, and protrude about 2 mm into the vitreous humour so as to fully expose the sensor (e.g. sensing capacitor) within the vitreous humour. Although in some embodiments, the width and thickness may be about the same the width may be independent of thickness. For example, in some embodiments, the sensor device may have a thickness less than a width so as to maximize the circuit area of an integrated circuit wafer of the sensor device.

The first and second wafers may be formed from substrate materials having matched or unmatched temperature coefficients of expansion. Further, if both wafers have different coefficients of thermal expansion at least one stress isolation feature may be incorporated into the first wafer to mechanically decouple the pressure sensor from the second wafer. Typically, all electrical connections are located on a bottom or back side of the first and second wafers so as to provide an appropriate electrical interface between the transducer (capacitive device) and the input stage of signal conditioning electronic or between the inductive device (coil) and the input/output of the telemetry circuit transferring data and power with the external acquisition system.

As discussed above, the vertical stacking of the wafers is configured to create a hermetically sealed cavity between the first and second wafers. In one example, a sealing ring is disposed between the first and second wafers and is configured to hermetically seal the first and second wafers. A dielectric layer may be disposed over the implantable device to electrically isolate and encapsulate the first and second wafer and provide an adhesion layer. Additionally or alternatively, a titanium barrier may be disposed over the dielectric layer or the implantable device so as to further hermetically encapsulate the first and second wafers. A biocompatible polymer coating may be disposed over the titanium barrier. The present invention provides redundant hermetic sealing to ensure chronic implantation so as to provide long-term stable and continuous IOP measurements and profiles for time periods of months to years (e.g., 1, 5, 10, or 15 years). Due the potential impact on the sensitivity of the transducer, the thickness of the layers deposited or coated on top of the sensing area with the diaphragm should be controlled and/or minimized (e.g. thinner oxide, Ti layer and functionalized polymer layer). This is not the case in other areas, such as a Reference capacitor and inductive antenna coil (e.g. differential dipole), which do not present mechanical sensitivity and designed to address required electrical characteristics (e.g. shunt capacitor, etc.).

A vertically stacked implantable device for directly measuring an IOP of an eye comprises a first wafer and a second wafer. The first wafer comprises at least a pressure transducer configured to directly measure the IOP of the eye. The second wafer comprises at least a digitizing integrated circuit. The first wafer is vertically stacked or disposed over the second wafer. The implantable device is sized or shaped to be positionable within a vitreous body of an eye so as to measure the IOP of a vitreous humour.

At least one power receiving and/or data transmission coil is vertically stacked or disposed over the first wafer and a second cavity of the pressure transducer (e.g., reference diaphragm) while a first cavity of the pressure transducer (e.g., sensing diaphragm) remains exposed. Typically, the pressure transducer has an operating range from −150 mmHG to 250 mmHG around atmospheric pressure (also called common mode of full scale) which will measure a gauge pressure of 0 to +30 mmHg (defined as absolute IOP pressure minus the external atmospheric pressure, more particularly in a common mode range from −100 mmHG to +200 mmHG. In some embodiments, an interposer may be disposed below the second wafer. The interposer comprises anchoring means, a distal tissue penetrating tip, and/or an extraction feature. The interposer can also be configured as a bottom wafer acting a boat layer or support adapted to support or hold the 3D stack of wafers, such as the four wafer design described herein (e.g. MEMS/ASIC/Supercap/Battery). In some embodiments, the boat layer is included as a mechanical layer which functions to anchoring the stack to the sclera and is not required to provide any electrical function. The interposer may further comprise at least one capacitor for supplemental energy storage and/or at least one coil configured to receive power and/or transmit data. This super-capacitor may be defined with dielectric layer and top/bottom plates that could be defined with multiple layers to increase area capacitance density.

An injectable intraocular pressure sensor system comprises a fluid-filled syringe or injector and an implantable IOP sensor device. The IOP device comprises a first wafer and a second wafer. The first wafer comprises at least a pressure transducer configured to directly measure the intraocular pressure of the eye. The second wafer comprises at least a digitizing integrated circuit. The first wafer is vertically stacked or disposed over the second wafer. The injector or syringe comprises a gauge of 19 or higher and may be filled with biocompatible fluids, such as saline and the like.

The details of one or more implementations are set forth in the accompanying drawings and the description below. Other features will be apparent from the description and drawings, and from the claims.

BRIEF DESCRIPTION OF THE DRAWINGS

FIGS. 4D and 4E illustrate an example coil and an overview of the implantable device of FIG. 1A depicting the locations of various components, respectively.

DETAILED DESCRIPTION OF THE INVENTION

Figure 1A:
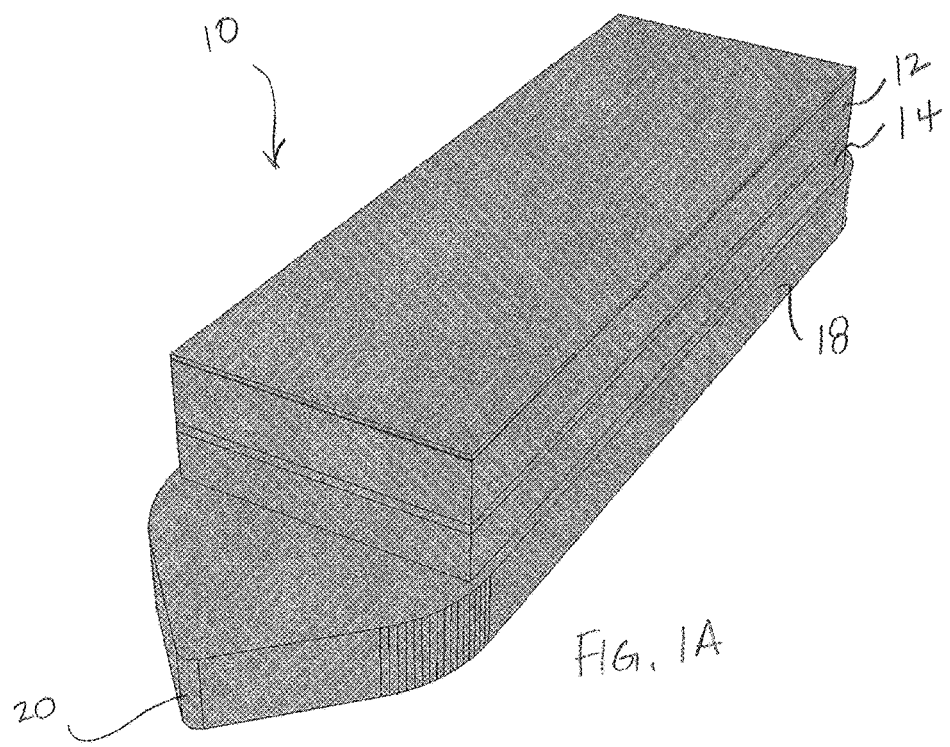
FIGS. 1A through 1D are isometric views of a vertically stacked implantable device according to embodiments of the present invention.
Figure 1B:
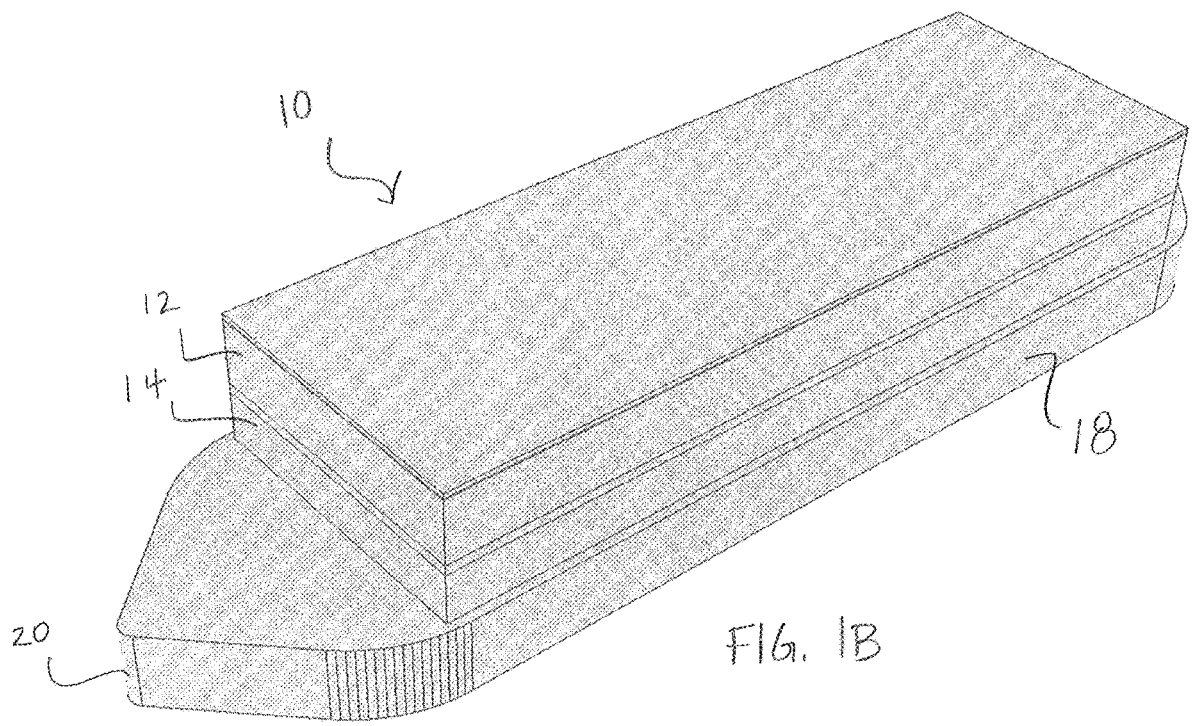
Figure 5:
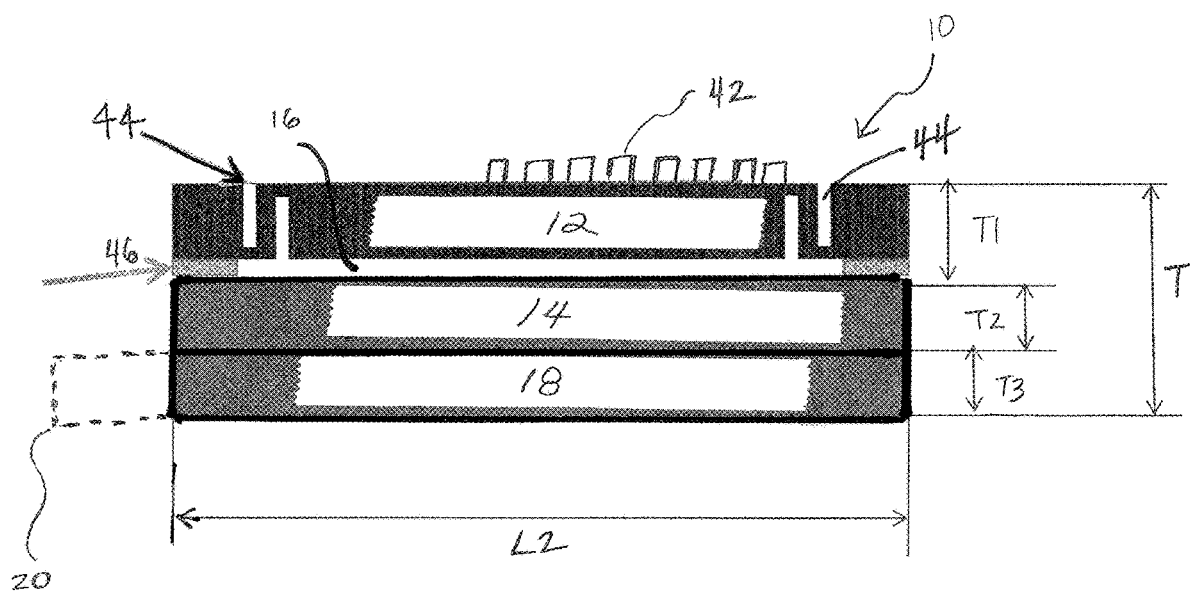
FIG. 5 illustrates a cross sectional side views of the vertically stacked implantable device of FIG. 1A with power receiving and/or data transmission coil.
Figure 7A:
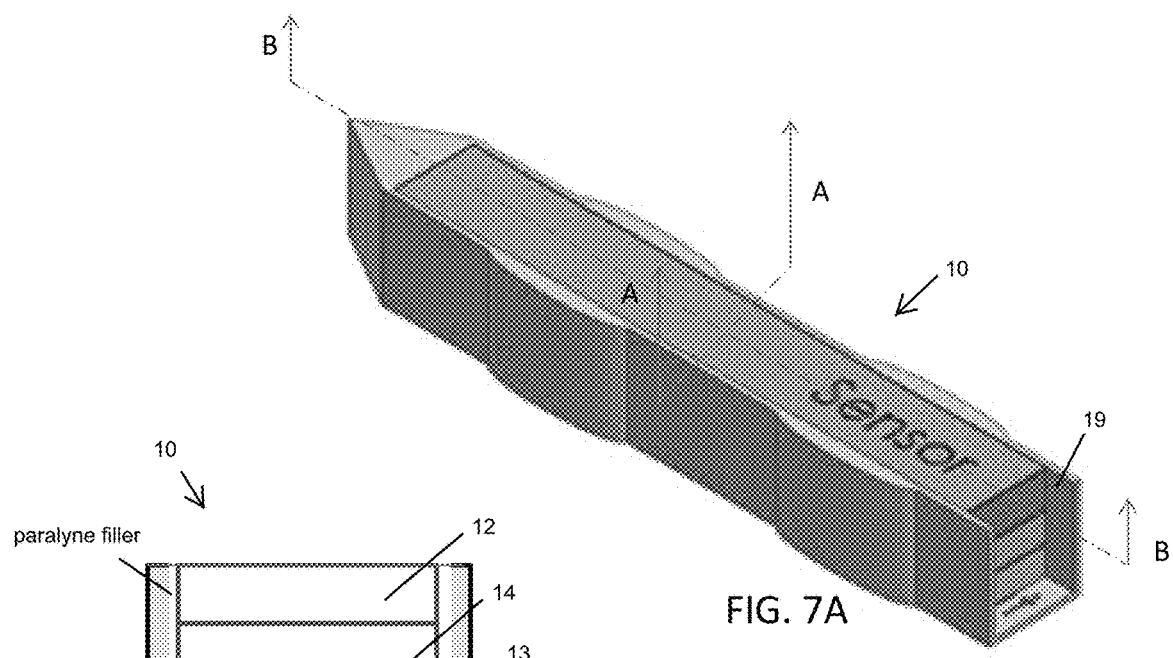
FIGS. 7A-7C illustrate several views of an alternative design of a vertically stacked implantable device according to embodiments of the invention.
Figure 7B:
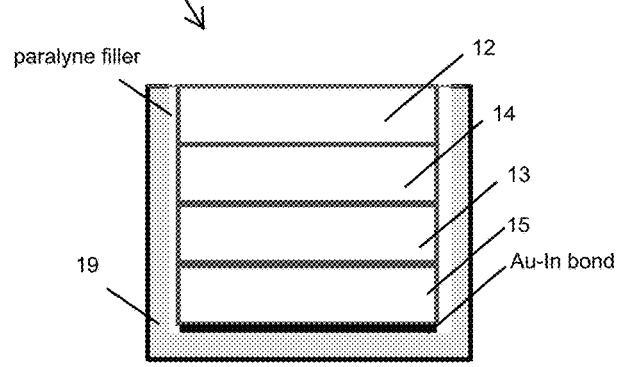
Figure 7C:
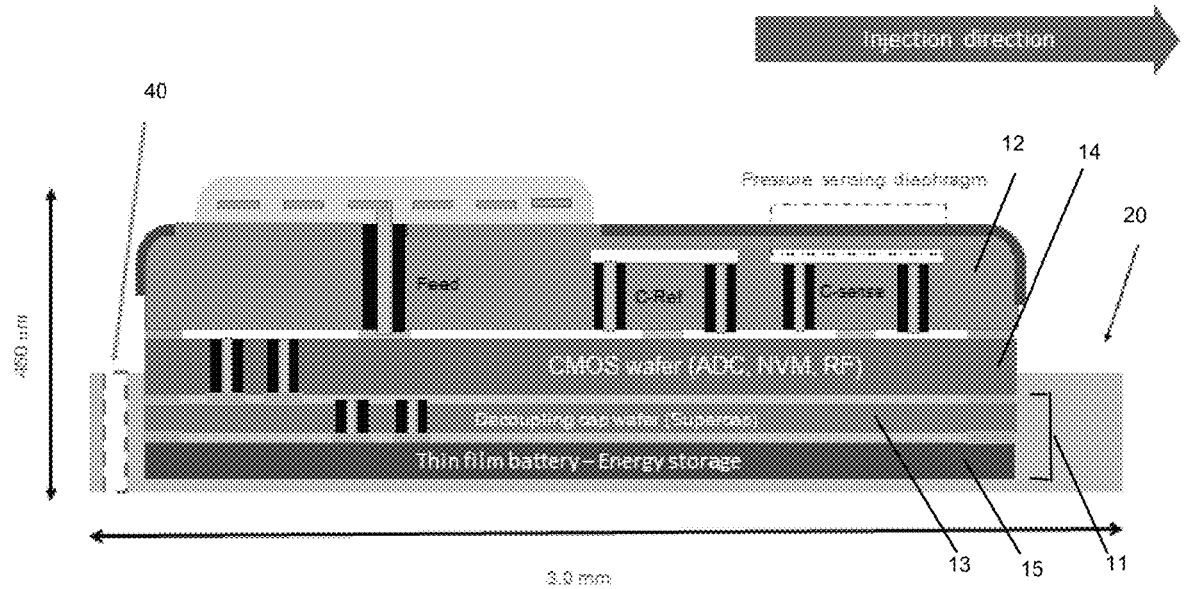
Figure 8A:
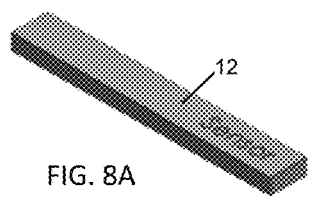
FIGS. 8A-8E illustrate a fabrication process for a sensor device in accordance with embodiments of the invention.
Figure 8B:
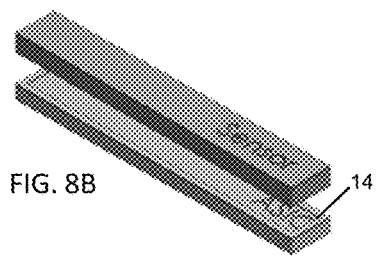
Figure 8C:
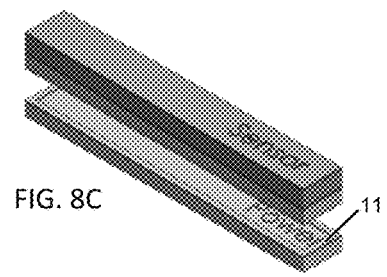
Figure 8D:
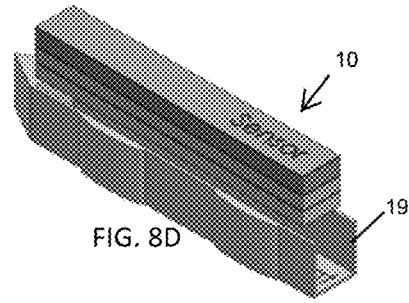
Figure 8E:
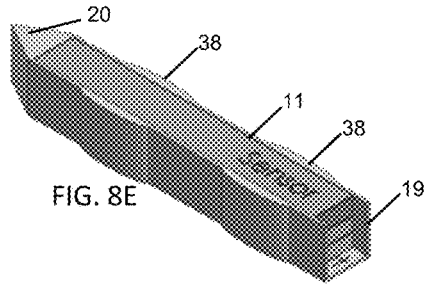

Embodiments of the present invention provide improved MEMS based pressure sensor implants for accurate and continuous measurement of IOP that can be beneficial in the treatment of eyes, for example beneficial in the treatment of glaucoma. FIGS. 1A and 1B illustrate isometric views of a vertically stacked implantable pressure sensor device 10 for measuring IOP according to embodiments of the present invention. The implantable device 10 comprises vertically stacked heterogeneous components, namely a first MEMS wafer or die 12 and a second CMOS wafer or die 14. The first wafer 12 comprises at least a pressure sensor configured to measure IOP on a frequent or desired basis (e.g., 1 sample per hour, 2-4 samples per day, etc.). The second wafer 14 comprises at least a digitizing ASIC. In some embodiments, the ASIC includes a microcontroller to enable firmware update of the implant, customization of sampling function (rate/window, accuracy, resolution, etc), auto-adaptative sampling to measured pressure, built-in self-test, error detection and correction, embedded diagnostics, broad use models with on-demand sample, streaming data and autonomous mode. The first MEMS wafer 12 is vertically stacked or disposed over the second CMOS wafer 14 so as to form a first hermetic seal. In particular, the vertical stacking of the wafers is configured to create a hermetically sealed cavity 16 (as shown in FIG. 5) between the MEMS 12 and CMOS wafers 14 of the implantable device 10. In some embodiments, the stack includes one or more additional wafers, for example one or more wafers adapted for use as a power source. Such embodiments may include a third wafer that includes a supercapacitor. In some embodiments, the stack further includes a fourth wafer that includes a battery. Such embodiments may utilize a power management scheme switching between the supercapacitor and battery in order to prove more efficient power discharge from a high impedance thin-film battery, such as a LiPON battery. An example of such a configuration is shown in the embodiment in FIG. 7A. As can be seen in the cross-sections A-A and B-B in FIGS. 7B and 7C, respectively, the stacked sensor device of FIG. 7A includes the MEMS 12 and CMOS wafers 14, a decoupling capacitor wafer 13 and a thin film battery/energy storage wafer 15. In one aspect, the wafers of the stack may be bonded together with low temperature Gold-Indium (Au—In) bond, while the cavities are formed using a silicon-to-silicon fusion bond. This configuration provides improved thermal budget management, while the silicon-to-silicon fusion bond provides long term vacuum stability (e.g. greater than 20 years). In this embodiment, rather than an interposer layer 18, the stacked device is placed within a support structure or boat 19.

This approach of wafer or die stacking is sometimes referred to as "chipscale packaging" within the electronics manufacturing field. Chipscale packaging is well understood by those of skill in the art in the MEMS/CMOS manufacturing industry, and is of particular benefit to the present invention in enabling production of smaller, integrated wafer assemblies that are easier to manufacture, provide improved performance, and are less expensive. In particular, constructing the implantable device 10 based on this vertical stacking approach allows for the implant form factor (e.g., dimension, size, shape, volume, etc.) to be significantly reduced (e.g., by a factor of 10×). Conventional implants typically require titanium, ceramic, glass or like outer packaging, which adds to the overall size and bulkiness of such conventional implants. The present invention advantageously employs vertical stacking to define its own hermetic package, which encapsulates all the electronics. As such, the implant 10 architecture and resulting form factors allow it to be easily implanted as an injectable and within a desired location within the eye of a patient.

Figure 1C:
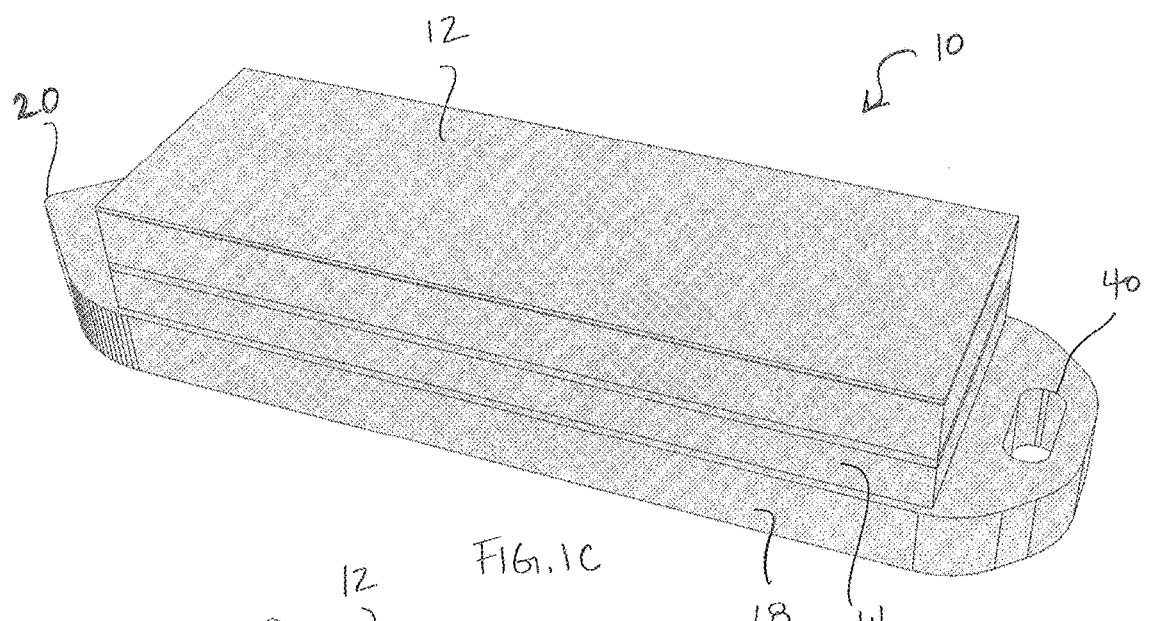
Figure 1D:
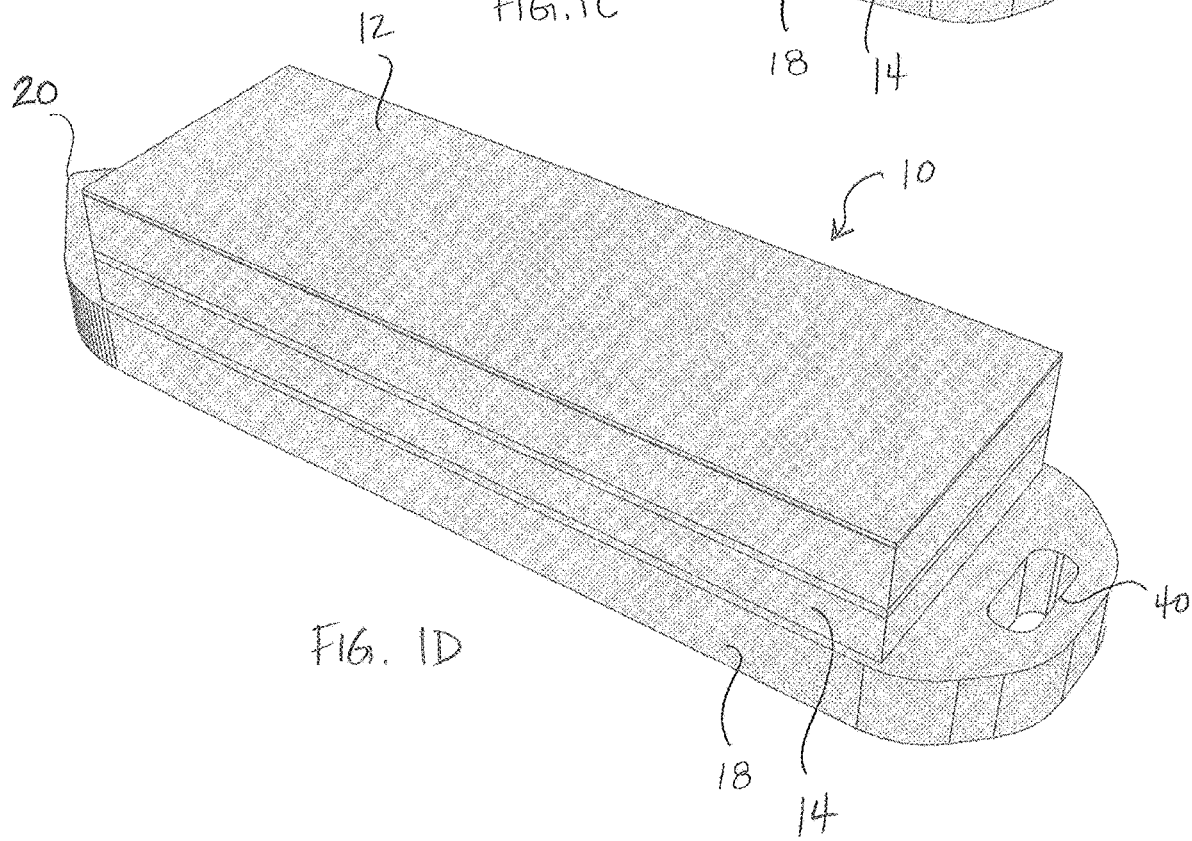

As described in greater detail in co-pending U.S. Non-Provisional patent application Ser. No. 14/789,491 (now U.S. Pat. No. 10,213,107), the implantable device 10 is sized and/or shaped to be positionable within a vitreous body of an eye so as to measure an IOP of a vitreous humour. It will be appreciated however that the implant may be positioned in alternative eye structures, such as the anterior chamber, posterior chamber, suprachoroidal space, sclera, and/or cornea, or in other anatomical locations outside the eye for measurement of physiological signals other than IOP. As shown in FIGS. 1C and 1D, an anchoring interposer wafer or die 18 may be disposed below the CMOS wafer 14. The interposer 18 may have a distal tissue-penetrating tip 20 to help facilitate final positioning of the implant device 10 within the vitreous body to minimize trauma and/or formation of scar tissue at the site of implantation.

Figure 1E:
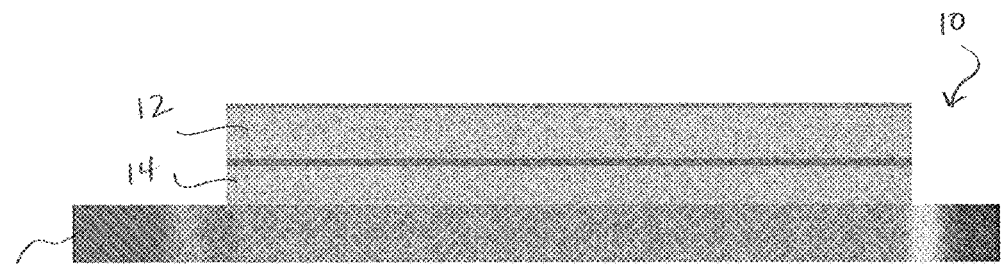
FIGS. 1E and 1F illustrate cross sectional side views of the vertically stacked implantable device of FIG. 1A.
Figure 1F:
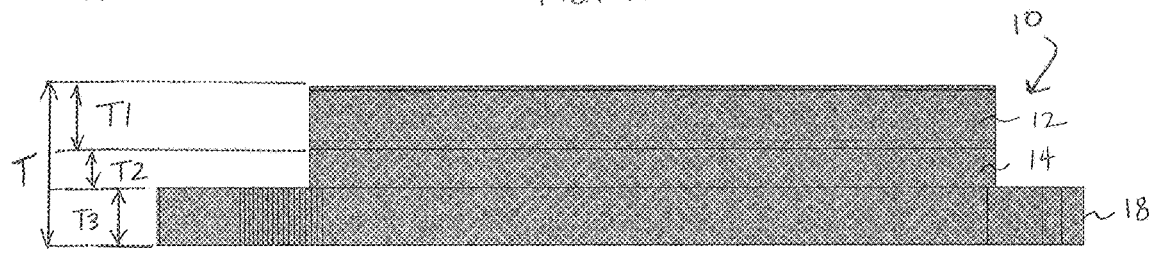
Figure 1G:
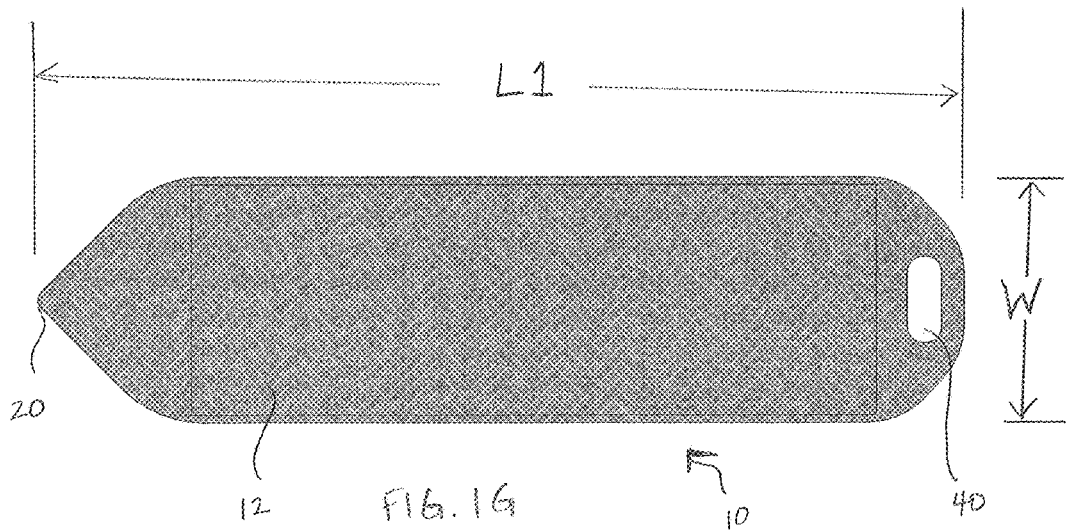
FIG. 1G illustrates a top view of the vertically stacked implantable device of FIG. 1A.

Referring to FIGS. 1E and 1F, cross sectional side views of the vertically stacked implantable device 10 are shown while FIG. 1G illustrates a top view. Generally, the implantable device 10 is dimensioned (e.g., thickness, width) to correspond to an inner diameter of a syringe having a gauge of 19 or higher for injectability purposes. Further, the implantable device 10 is generally dimensioned (e.g., length) so as to allow the implanted device 10 to reach the desired sensing location through the tissue thickness from where it is anchored. For example, positioning the implantable device 10 within the vitreous body and anchoring the implant against the sclera requires an implant length of about 4 mm. Generally, the implantable device 10 may comprise a maximum thickness T of about 690 microns or less, a maximum length L1 of about 4 mm or less, and a width W of 690 microns or less. In particular, the device without the interposer wafer 18 may have a maximum length L2 of about 4 mm or less (FIG. 5). The MEMS wafer 12 may have a greater thickness than the ASIC wafer 14 and/or interposer wafer 18 so as provide for sufficient rigidity of the pressure sensor. Alternatively, each wafer may have substantially the same thickness. The MEMS wafer 12 may have a first thickness T1 of about 200 microns or less, the ASIC wafer 14 may have a second thickness T2 of about 200 microns or less, and the interposer wafer 18 may have a third thickness T3 of about 200 microns or less.

Figure 2A:
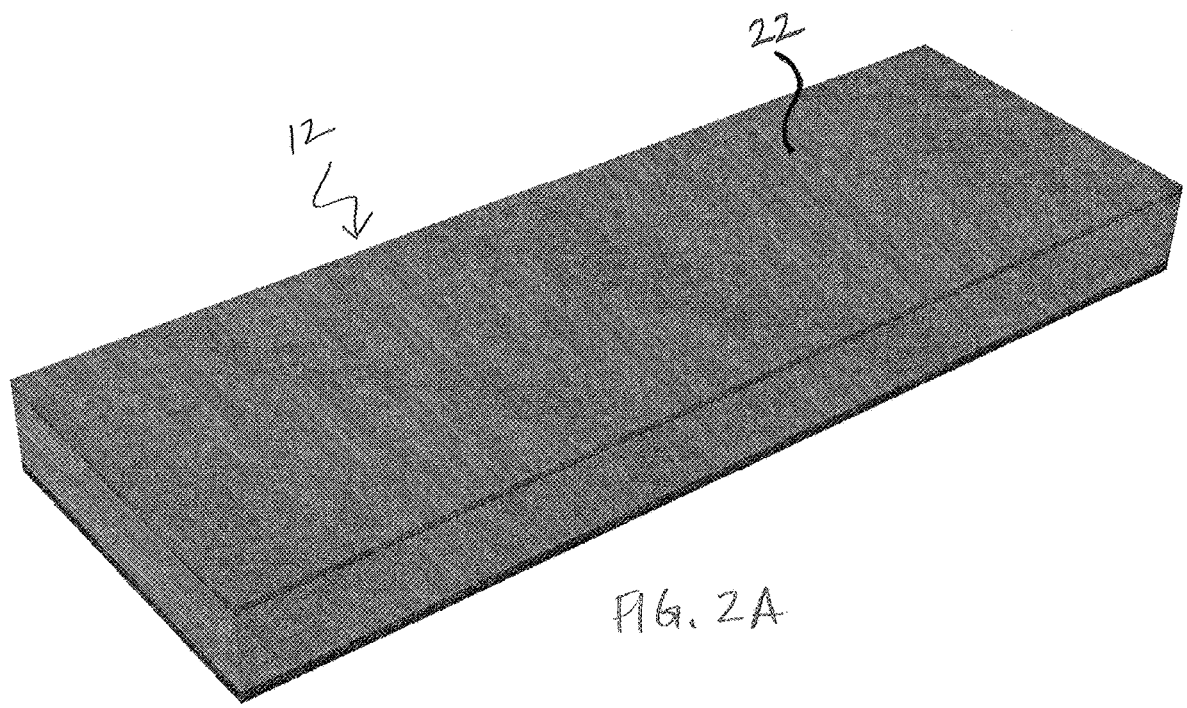
FIGS. 2A and 2B illustrate top views of a MEMS based pressure sensor of the implantable device of FIG. 1A with and without a membrane layer.
Figure 2B:
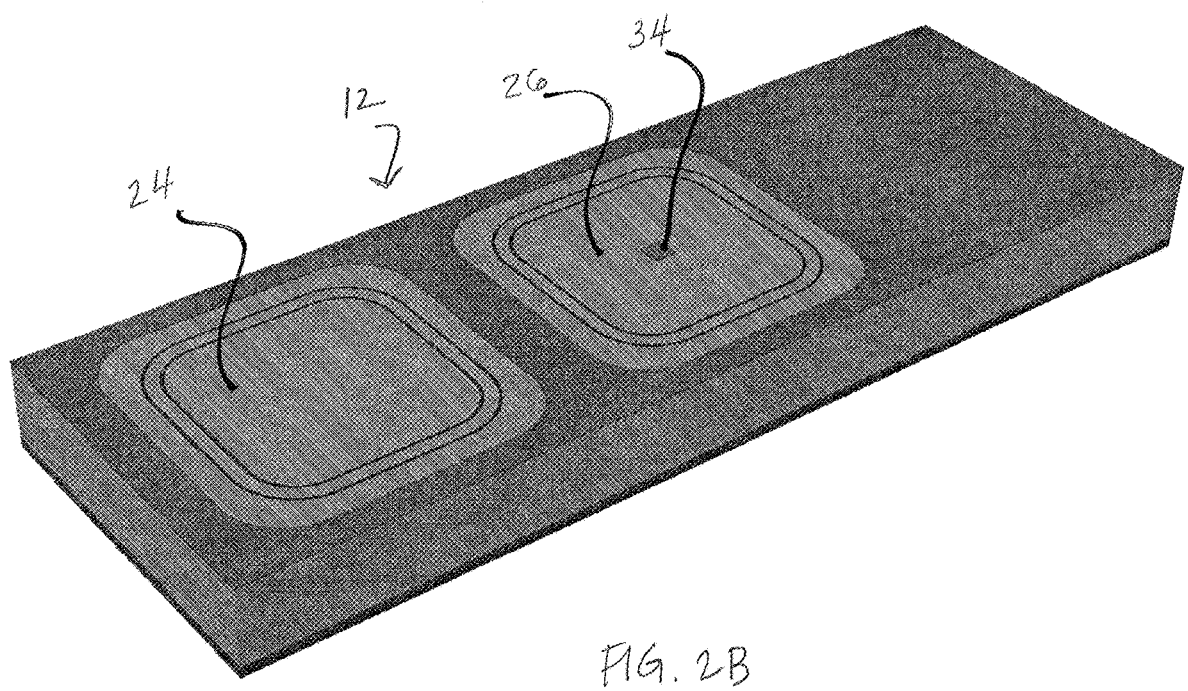
Figure 2C:
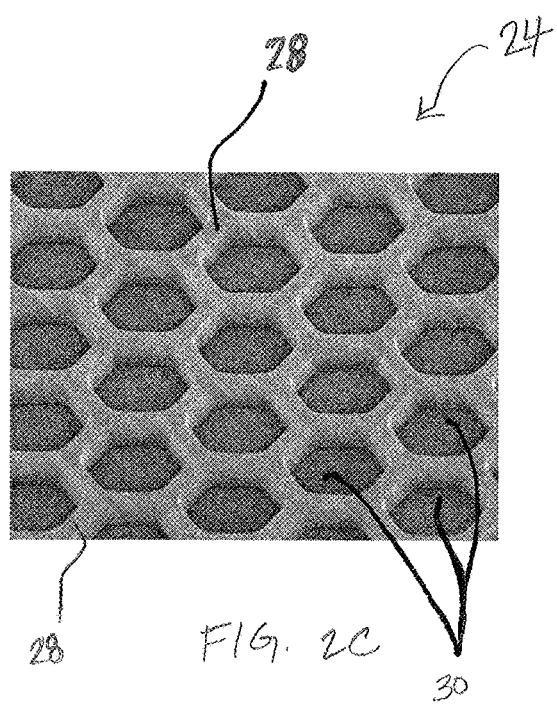
FIG. 2C illustrates a MEMS capacitive pressure transducer of the implantable device of FIG. 1A.
Figure 2D:
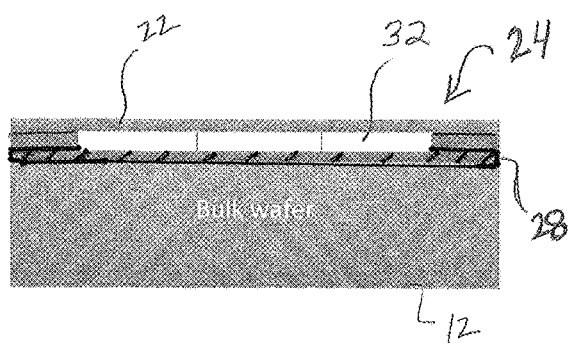
FIG. 2D illustrates a cross sectional view of the MEMS capacitive pressure transducer of the implantable device of FIG. 1A.

Referring to FIGS. 2A and 2B, the pressure sensor 12 of the implantable device 10 may comprise an active electrode in the form of a capacitive pressure transducer. FIG. 2A illustrates a top view of the MEMS wafer 12 of the implantable device 10 with a diaphragm membrane layer 22, while FIG. 2B illustrates the MEMS wafer 12 with the diaphragm membrane layer 22 removed. The capacitive pressure transducer comprises at least a first cavity structure 24 (e.g., sensing capacitor) and a second cavity structure 26 (e.g., reference capacitor), wherein the sensing capacitor 24 is distal of the reference capacitor 26. As shown in FIGS. 2C and 2D, the sensing capacitor 24 (or reference capacitor 26) may comprises a base honeycomb structure 28 having multiple cavities 30 (e.g., 4 to 6 cavities) so as to increase the surface area available for measurement and reduce internal stress areas.

Figure 10A:
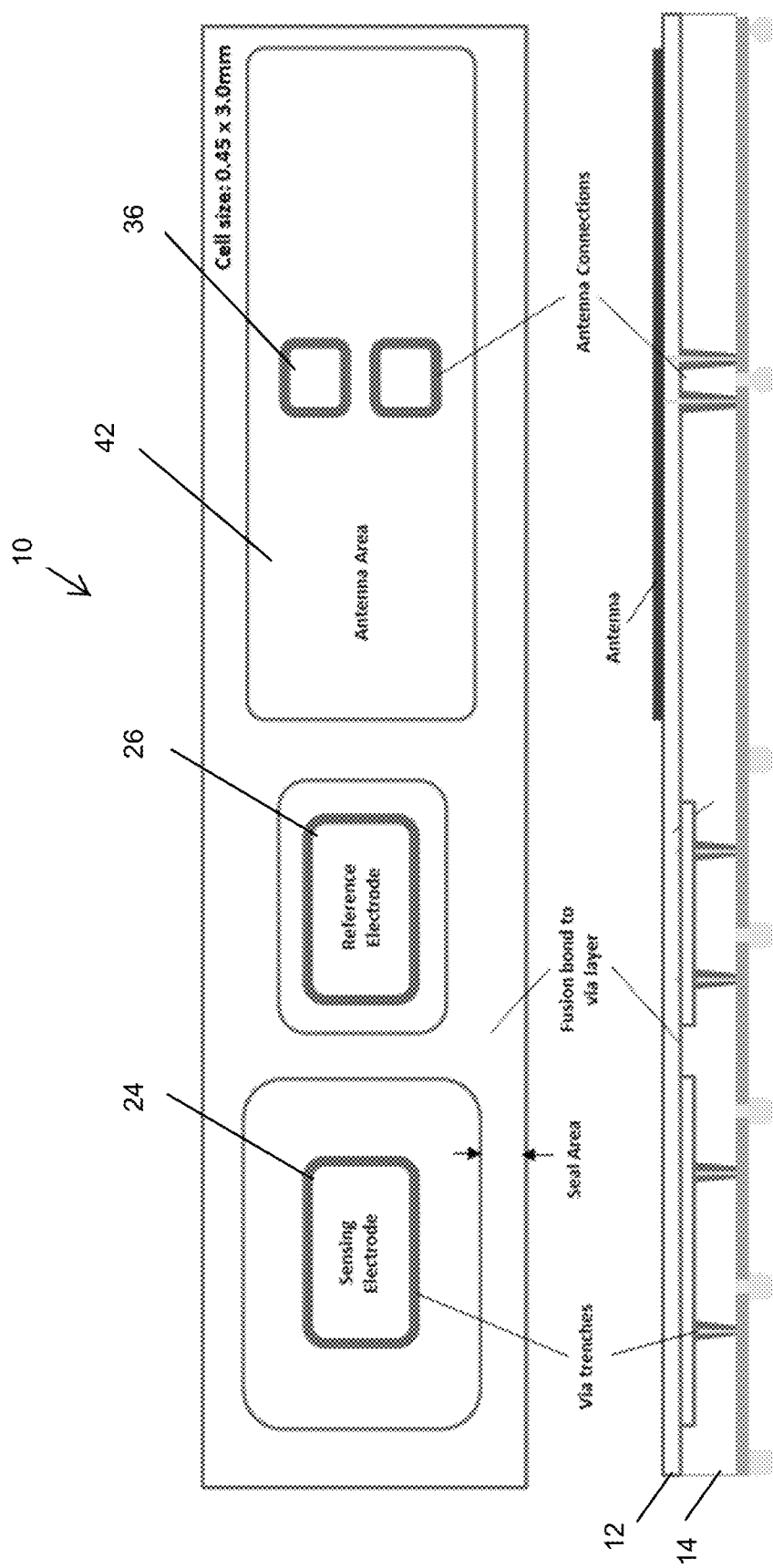
FIG. 10A-B illustrate a schematic of a reduced width design of a sensor device in accordance with embodiments of the invention.
Figure 10B:
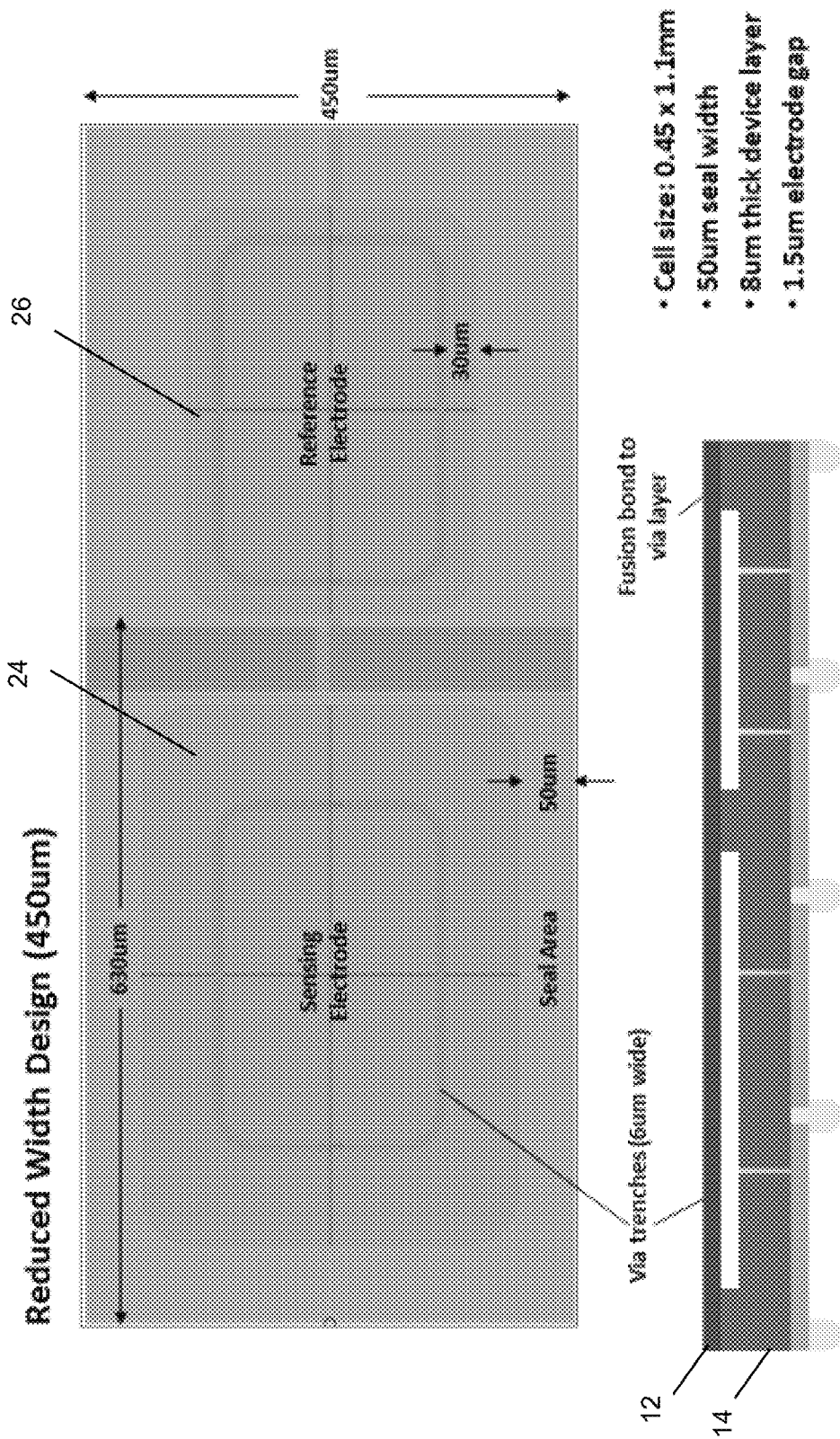
Figure 10C:
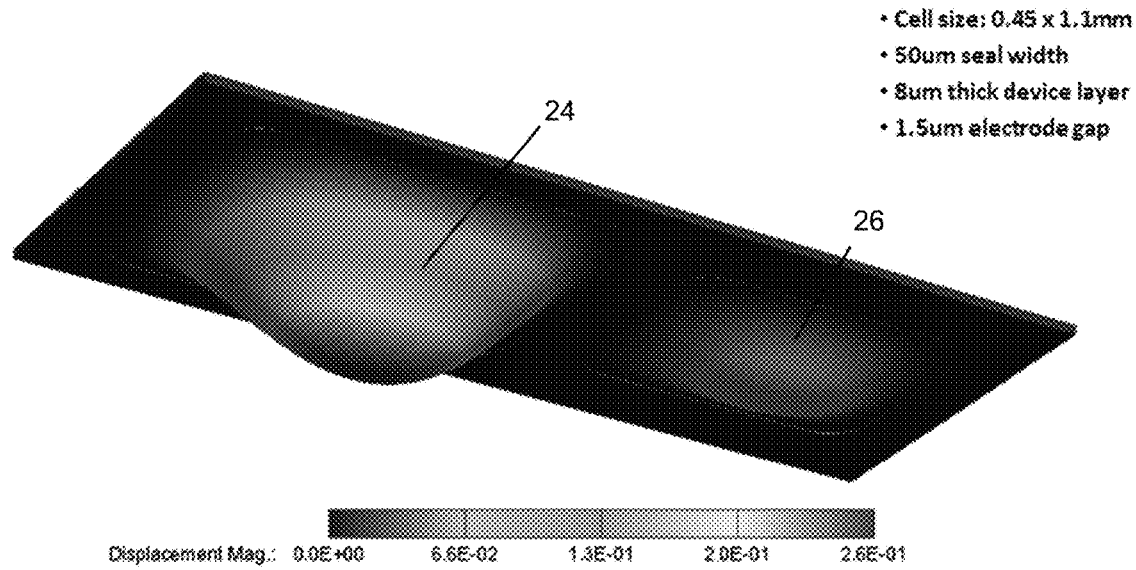
FIG. 10C illustrates a displacement model of a membrane of the sensor and reference capacitors of the sensor device in FIG. 10A.
Figure 10D:
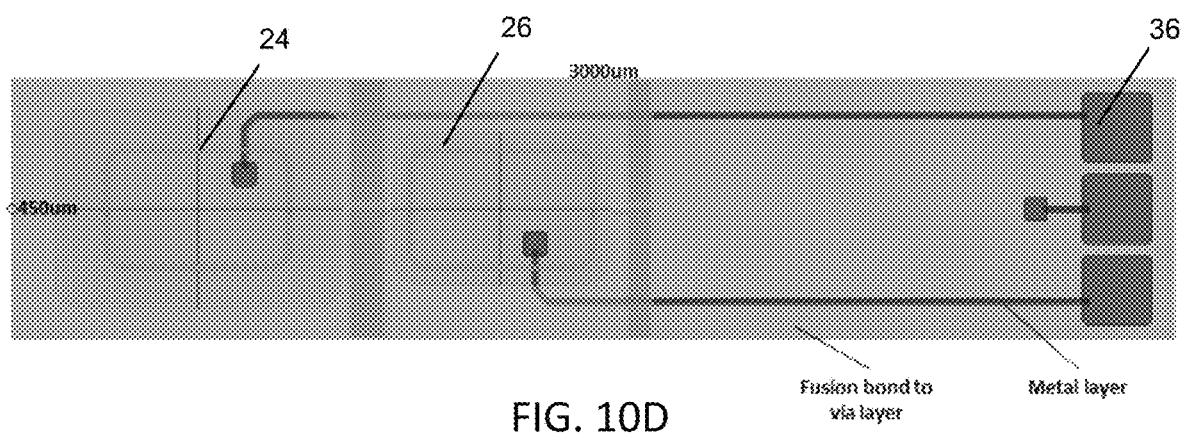
FIG. 10D illustrates a die design of the sensor device design in FIG. 10A.
Figure 11A:
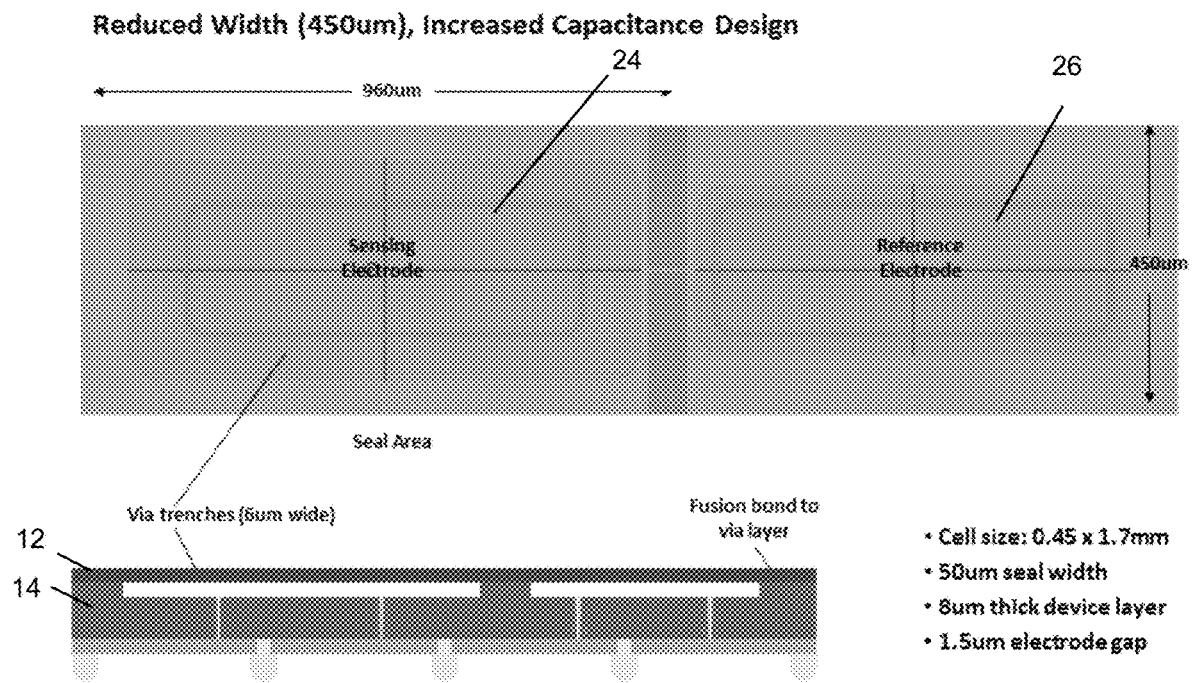
FIG. 11A illustrate a schematic of an alternative reduced width design of a sensor device in accordance with embodiments of the invention.
Figure 11B:
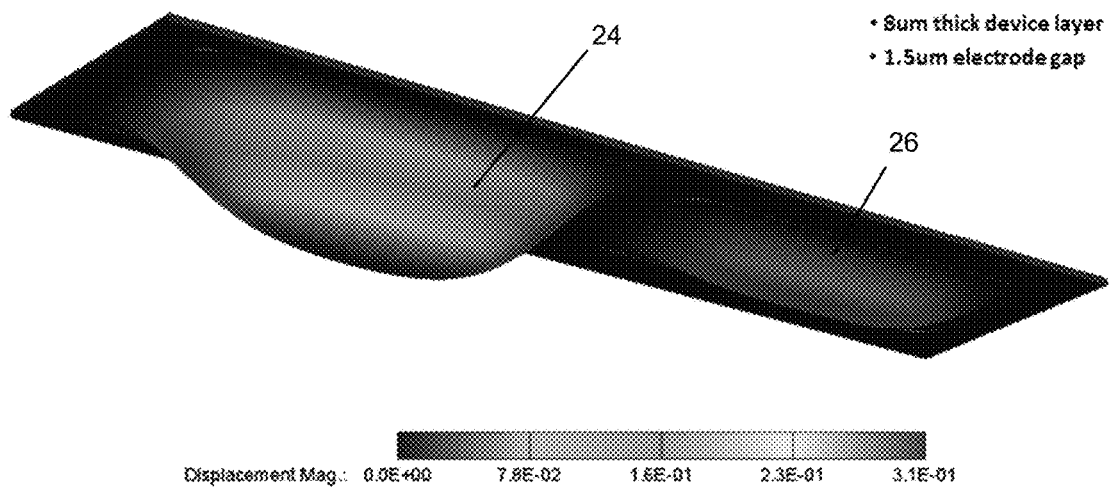
FIG. 11B illustrates a displacement model of a membrane of the sensor and reference capacitors of the sensor device of FIG. 11A.
Figure 12:
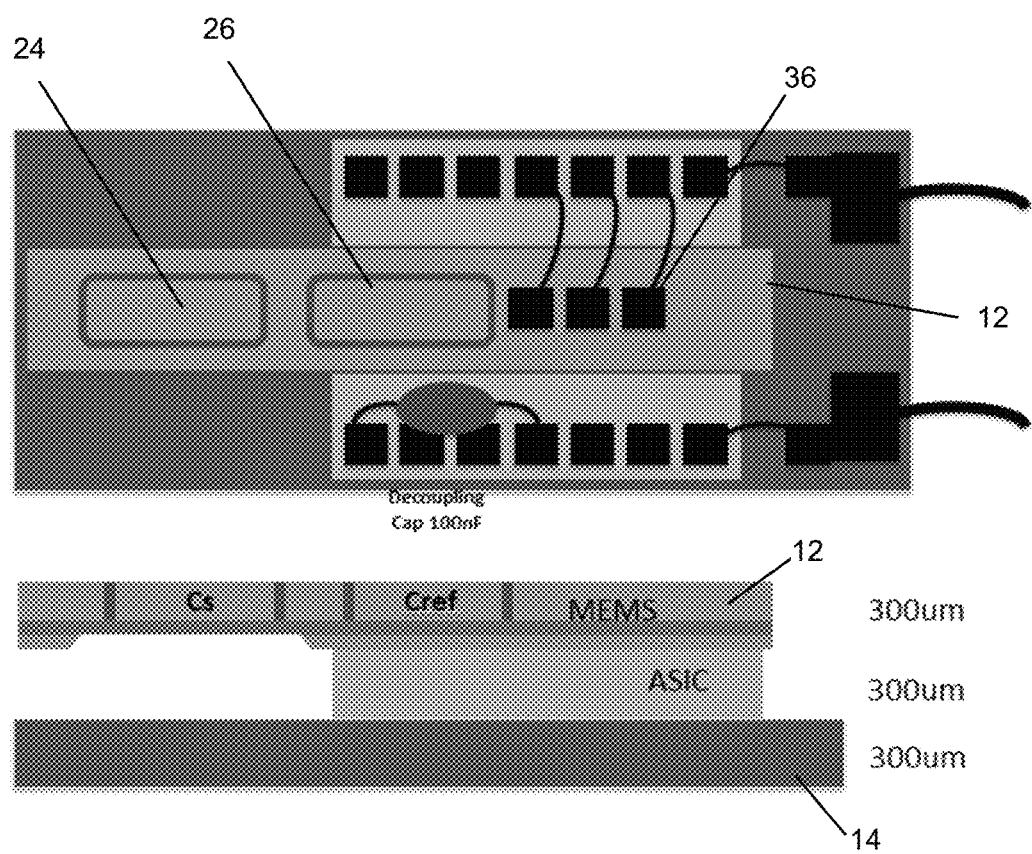
FIG. 12 illustrates a schematic of the electrical connections associated with a supercapacitor and thin-film battery layer of a sensor device comprised of vertically stacked wafers in accordance with embodiments of the invention.

Each cavity 30 of the sensing capacitor 24 is under vacuum 32 (e.g., gaseous pressure that is less then atmospheric pressure) through bonding of a SOI device layer so that deformation of the membrane 22 under vacuum provides an accurate IOP measurement. In some embodiments, the reference capacitor 26 is without vacuum (e.g., cavity filled with oxide) so as to measure a reference pressure of one more parameters other than the IOP (e.g., variations due to stress, temperature, etc.) so that it is independent of the actual IOP measured by the sensing capacitor 24. In other embodiments, both the sensing and reference cavities have a vacuum but are different mechanically. For example, in a reference capacitor 26 which also has a vacuum, in order to remove the sensitivity to pressure, the membrane can be made smaller to increase stiffness but the capacitance is the same for closer matching when used in differential mode ($C_{sense}/C_{ref}$). Examples of such configurations having reference electrodes of reduced width are shown in the embodiments of FIGS. 10A and 11A. It is appreciated that the dimensions shown in the embodiments in FIGS. 10A and 11A are merely examples of device dimensions and should be noted that such devices may be fabricated according to various other dimensions in accordance with embodiments of the invention. For example, any of the dimensions shown may be scaled upwards or downwards (e.g. by 5%, 10%, 20%, etc.) as desired for a particular application. As can be seen in the displacement models in FIGS. 10C and 11B, the membrane of the reference electrode of reduced width has increased stiffness such that its displacement in response to a change in pressure is considerably less than that of the pressure sensor electrode. The reference capacitor 26 is positioned within the vicinity of sensing capacitor 24 in order to accurately cancel out noise signals or other artifacts that alter the sensing measurements. Additionally, the reference and/or sensing capacitors 24, 26 may have a post 34 centered therein so as to prevent the top reference and/or sensing membranes 22 from contacting the base structure 28. The pressure transducer will have the sensing capacitor 24 and the reference capacitor 26 with a common node, such as the bulk wafer 12. Typically, the pressure transducer has a full scale range from −100 mmHg to 200 mmHg, compare to 1 Atm (760 mmHg), and more particularly in a range from 660 mmHg to 960 mmHg (absolute). FIG. 10D illustrates a die design schematic showing the electrical connections between the sensor and reference electrodes to the one or more power source/energy storage wafers.

Figure 3A:
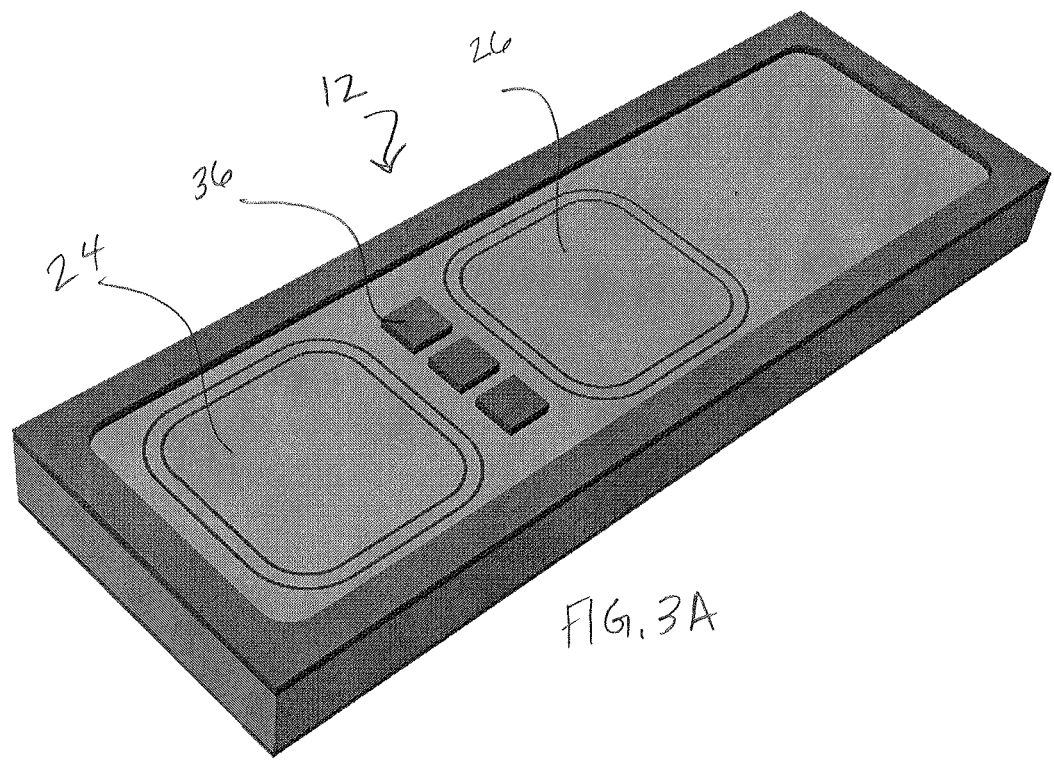
FIGS. 3A and 3B illustrate bottom view the MEMS based pressure sensor of the implantable device of FIG. 1A.
Figure 3B:
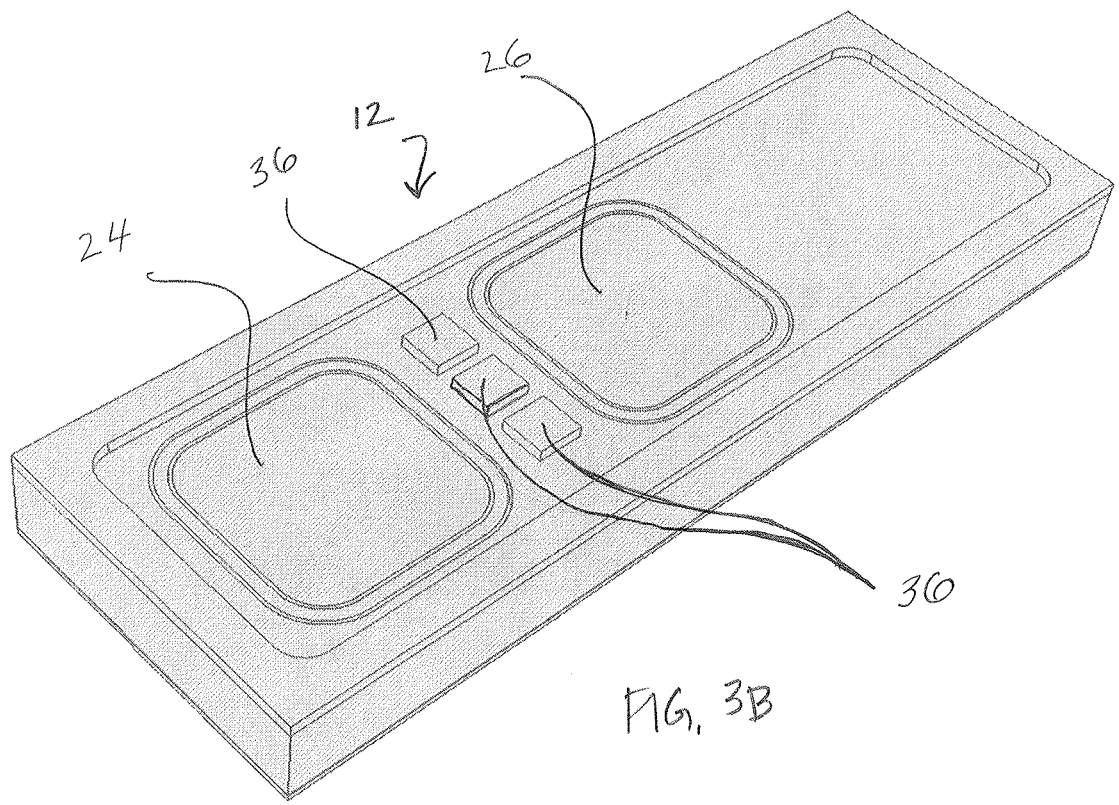

FIGS. 3A and 3B illustrate bottom views of the MEMS based pressure sensor 12 of the implantable device 10. In particular, electrical pads 36 provide a common node connection to electrically connect the MEMS wafer 12 to the ASIC wafer 14 to ground. Typically, vertical electrical connections (e.g., isolated through silicon via (TSV)) are provided between all components (e.g., pressure sensor 12, digitizing ASIC 14, and/or interposer 18) and are located on a bottom or back side of the wafers so as to provide an appropriate interface to a media (e.g., vitreous humour) to be measured and minimize parasitic effects.

Figure 4A:
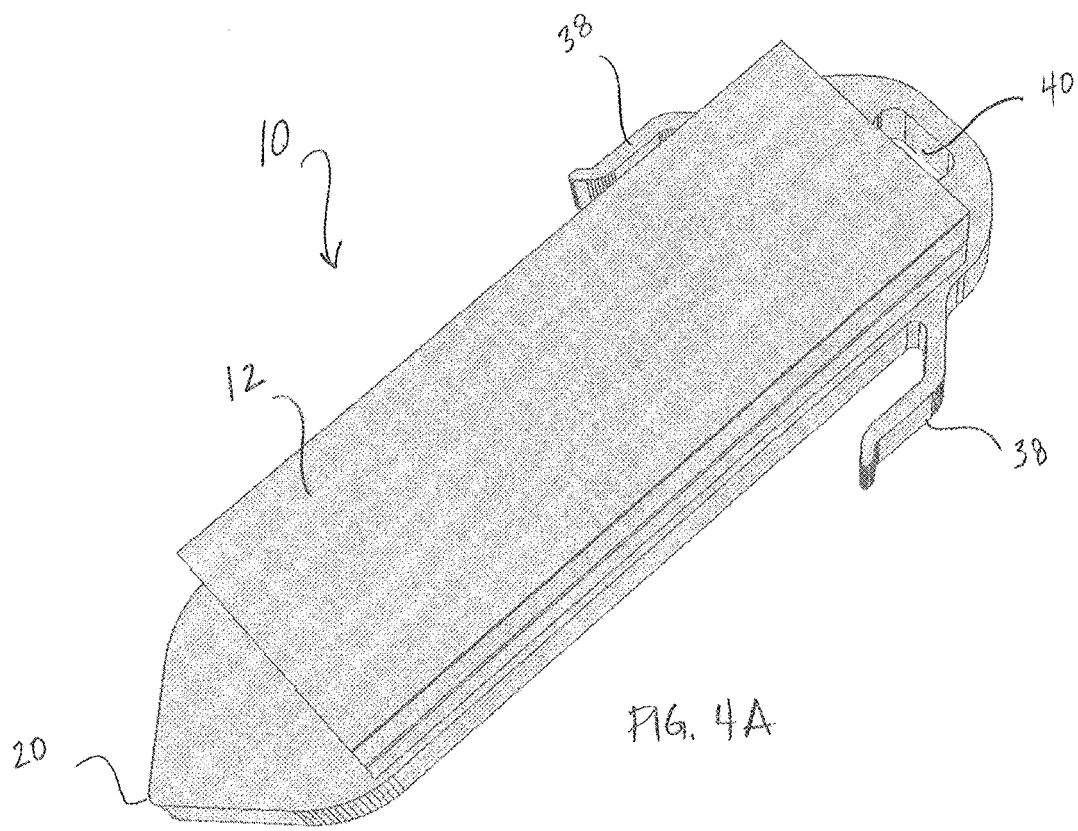
FIGS. 4A through 4C illustrate anchoring members of the implantable device of FIG. 1A.
Figure 4B:
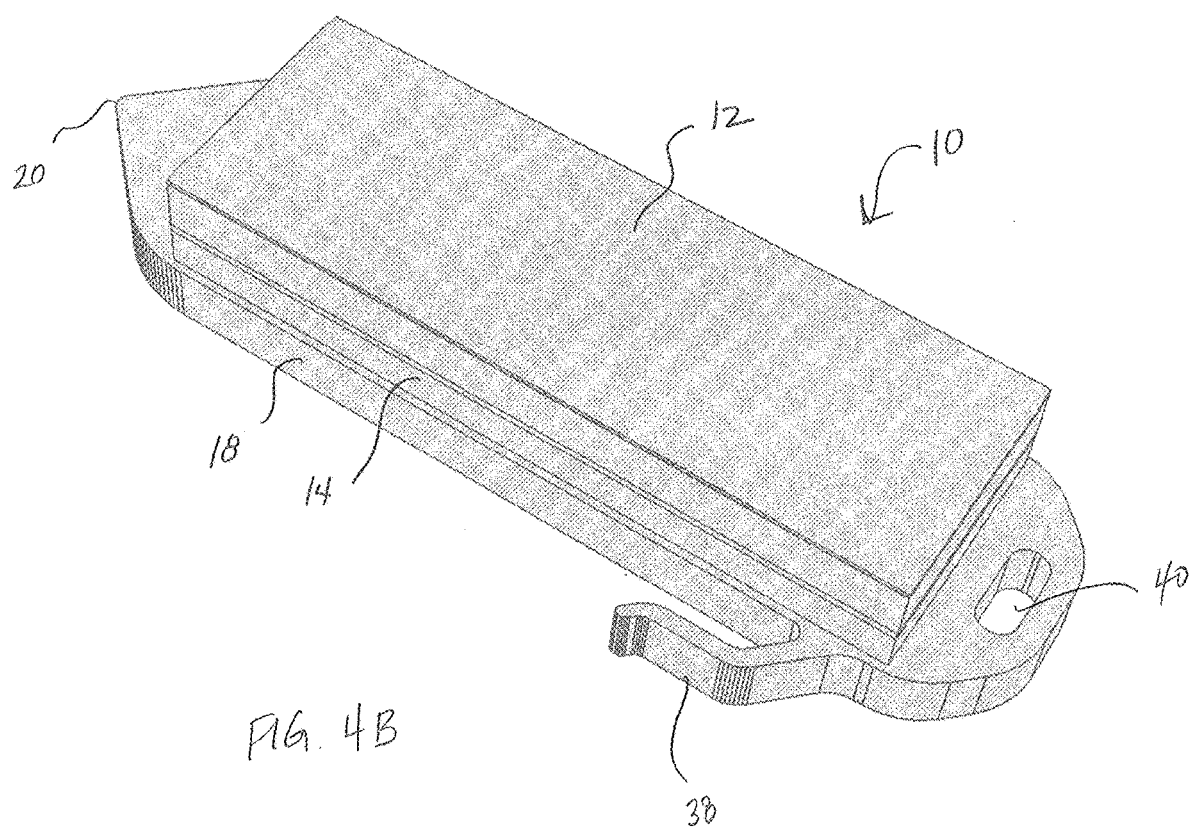
Figure 4C:
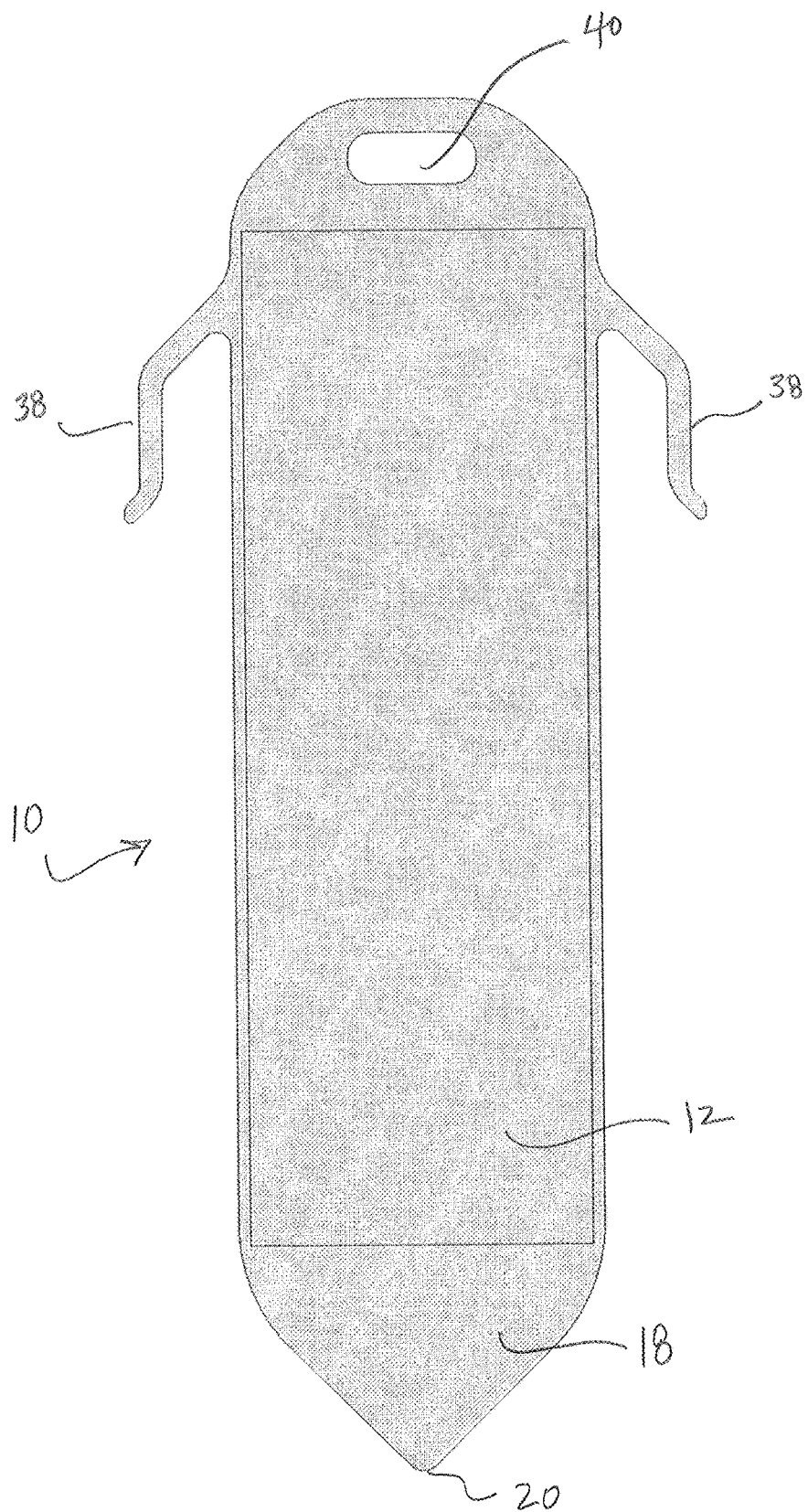

Referring now to the embodiments in FIGS. 4A through 4C, the anchoring interposer wafer 18 of the implantable device 10 is further illustrated. The anchoring wafer 18 may be disposed below the CMOS wafer 14 and comprise anchoring means 38, a distal tissue penetrating tip 20, and/or an extraction feature 40. The anchoring means 38 may comprise self-expanding anchoring legs, spring loaded fixation elements, or the like. The devices of the present invention may be temporary or permanent implants 10 that can be useful for both short term (e.g., days or months) and/or long term IOP monitoring of the eye (e.g., months to upwards of 10 years or more). In the case of short term monitoring or an adverse event, the implantable device 10 may be easily explanted via the extraction feature 40 on the anchoring wafer 18. The anchoring wafer 18 may further comprise at least one energy storage capacitor (29 in FIG. 4D) to extend energy storage of the implantable device 10 and/or at least one coil or antenna (not shown) configured to wirelessly receive power and/or transmit data with an external base station. The energy storage capacitor may be formed in the anchoring wafer or may be formed in separate layer or formed separately and attached to the device in various locations. It will be appreciated that the interposer wafer 18 may also be omitted from the implantable pressure stack 10 if it is directly incorporated within a therapeutic structure, such as implantable shunt, valve, stent, or drainage devices.

In some embodiments, the anchoring structure is formed in a separate support structure or "boat" in which the diced multi-wafer stack is placed and attached with low temperature metal alloy. An example of such a "boat" can be seen in the embodiment of FIG. 7A. In some embodiments, this support structure or boat may also include a distally tapered tip 20 to facilitate penetration through the sclera during implantation and may also include one or more anchoring features 38. Such features may be included as components with a mechanical function that clamps onto the sclera (e.g. a proximal and distal anchor on opposite sides of the sclera). The anchoring feature may also include an anchoring loop or extensions. Such anchoring features may be formed of Silicon, Titanium, shape memory alloy, or other suitable materials. In some embodiments, the boat is formed of a monolithic material and include side-walls that extend upwards, at least partly, along a thickness dimension of the stacked sensor device 10. The fabrication/assembly of a sensor device using a boat component having a distally tapered tip 20 and proximal and distal anchoring features 38 is illustrated in FIGS. 8A-8E.

Figure 9:
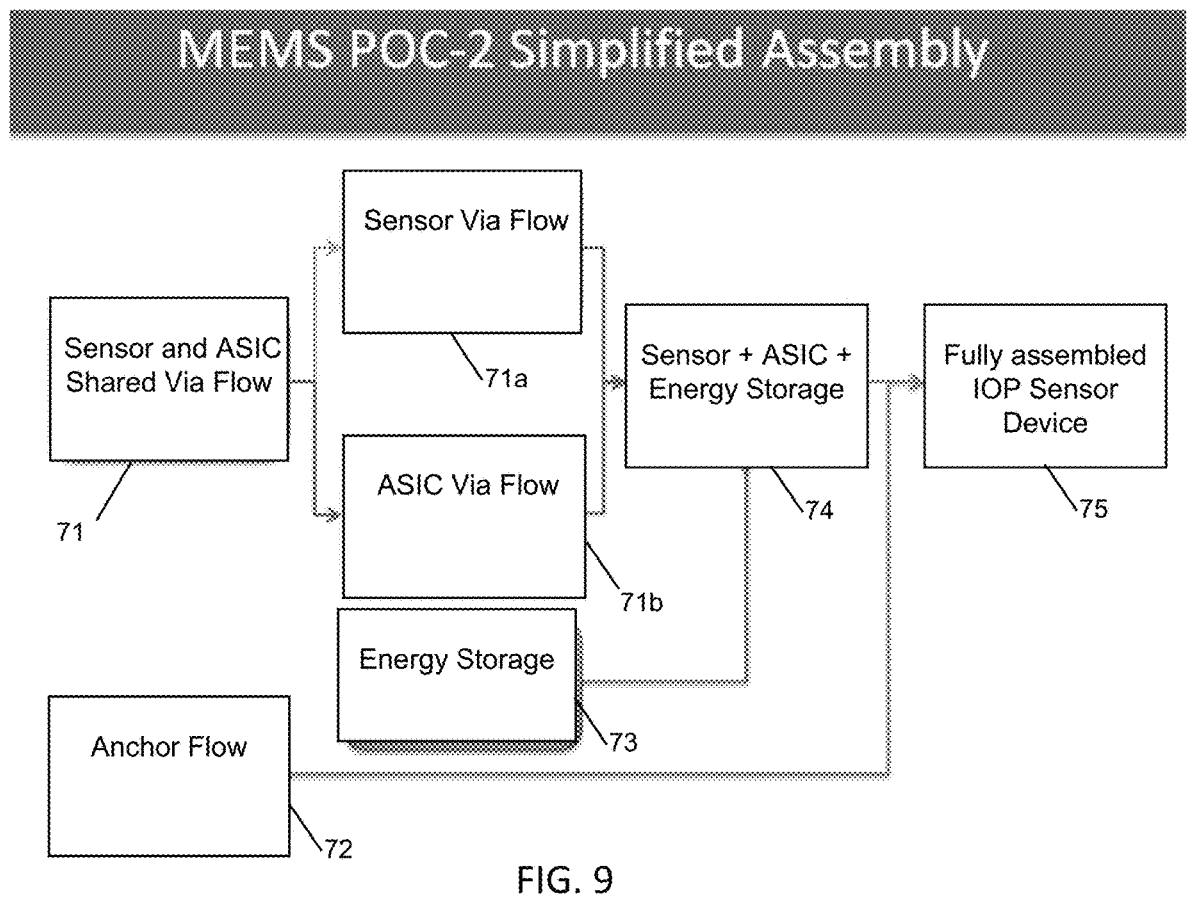
FIG. 9 illustrates a flowchart for assembly of a sensor device in accordance with embodiments of the invention.

A simplified flowchart of the assembly is shown in FIG. 9. In this method, the fabrication process flow for each wafer are performed and the wafer assembled in the sequence depicted. In this example, the sensor and ASIC may utilized a shared flow 71 or may utilize flows in parallel 71a, 71b, while the anchor structure flow 72 and the energy storage flow 73 are fabricated in separate process flows on separate structures or wafers. The sensor, ASIC and energy storage wafers are assembled 74 and assembled with the anchor structures to form the fully assembled IPO sensor device 75.

Referring now to FIG. 5, a cross sectional side view of the vertically stacked implantable device 10 is shown. In particular, at least one coil or circuitry 42 is illustrated for wireless charging of the battery-less implant and data communication with an external base station (e.g., glasses, phone, etc.). Details of the wireless interface are described in more detail in co-pending U.S. Non-Provisional patent application Ser. No. 14/789,942. In this figure, the least one coil 42 is vertically stacked or disposed over the first wafer 12 and the reference capacitor 26 while the distally positioned sensing capacitor 24 (FIG. 2B) remains exposed and entirely disposed within the vitreous body for accurate and direct IOP measurements. The coil 42 may be defined in terms of topology to provide the highest inductance, which is dependent on the depth of implantation and energy transfer efficiency. The first phase of operation may be recharging of the implant while the second phase may be data transfer to recover and record logged data. An overview schematic of the example implantable device of FIG. 1A is shown in FIG. 4E, which depicts the locations of the coil 42, reference capacitor 26 and sensing capacitor 36 on the device. It is appreciated that various other configurations may be used in accordance with the aspects of the present invention described herein.

As described above, vertical stacking of the implant 10 is configured to create a hermetically sealed cavity 16 between the MEMS and ASIC wafers 12, 14. For example, a gold sealing ring 46 or flange may be disposed between the first and second wafers to create this first hermetic seal between the MEMS 12 wafer and ASIC 14 wafer. The implant may further incorporate a second hermetic seal by depositing a dielectric layer, such as silicon dioxide, over the implantable device and a titanium barrier over the deposited dielectric layer for a third hermetic barrier. This redundant hermetic sealing ensures chronic implantation and provides enhanced sensing stability. Still further, a biocompatible polymer coating, such as parylene, polymethyl methacrylate (PMMA), and like polymers, may be disposed over the titanium barrier to minimize any immune system response (e.g., rejection of implant).

Figure 13:
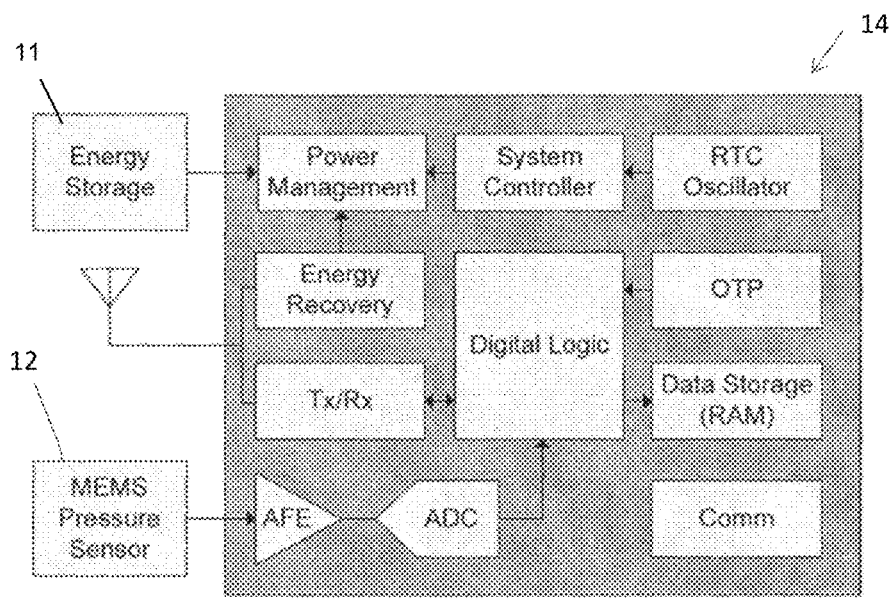
FIGS. 13 and 14 illustrate application specific integrated circuit (ASIC) block diagrams for sensor devices in accordance with embodiments of the invention.
Figure 14:
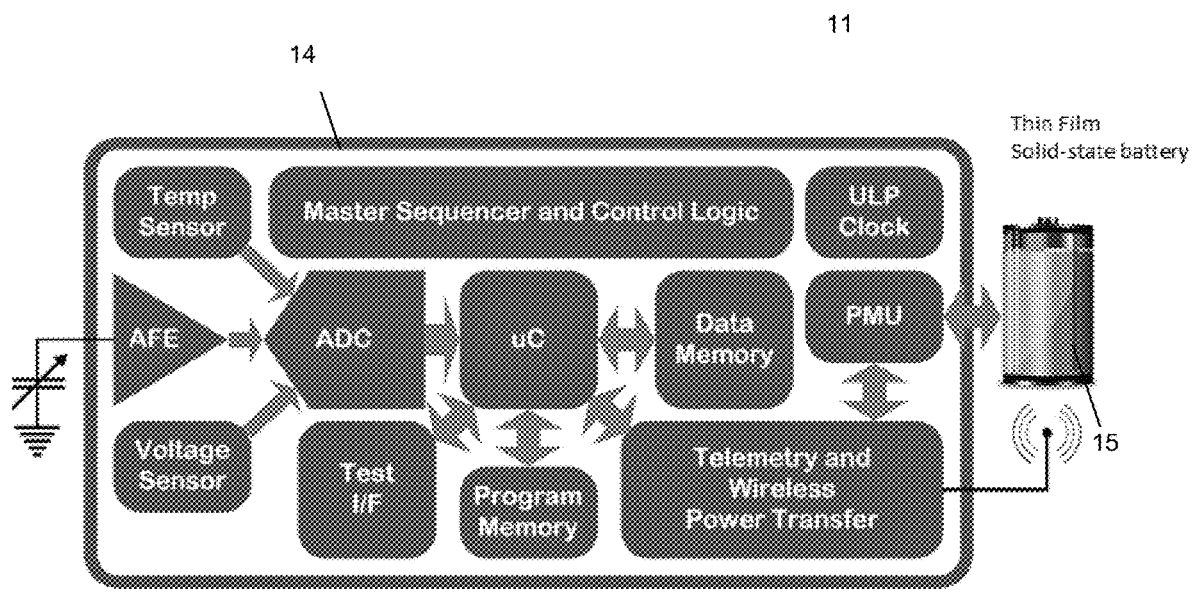

The ASIC wafer 14 may further comprise a radio frequency link, power storage, and/or data storage so as to maximize the wafer topology along its length and reduce the manufacturing complexity and costs of the stacked implant 10. FIG. 13 illustrates an ASIC block diagram illustrating the various functions of the ASIC wafer 14, such as signal processing, ADC, energy/power management, data acquisition and logging, radio frequency link, calibration, etc. The implantable device 10 may be entirely formed from the same substrate material, preferably silicon wafers or dies and have rounded or anti-traumatic edges to minimize any collateral tissue damage during positioning or implantation. The approach of using silicon material throughout the wafer stack (MEMS 12, ASIC 14, interposer 18) offers matching of the coefficient of thermal expansion (CTE) between the layers, which enables the mechanical stability of the overall implant 10 and reduces measurement drift. The pressure transducer 12 may also be embedded with mechanical stress isolation features 44 to decouple any intrinsic stress associated with the vertical stacking architecture, and in particular the TSV electrical connections and/or sealing ring 46. In particular, at least one stress isolation feature 44 may be incorporated into the MEMS wafer 12 to mechanically decouple the pressure sensor from the ASIC wafer 14. FIG. 14 illustrates a functional block diagram performed by the ASIC 14 in a sensor device equipped with a thin-film solid state battery 15 in accordance with embodiments described herein.

Figure 6A:
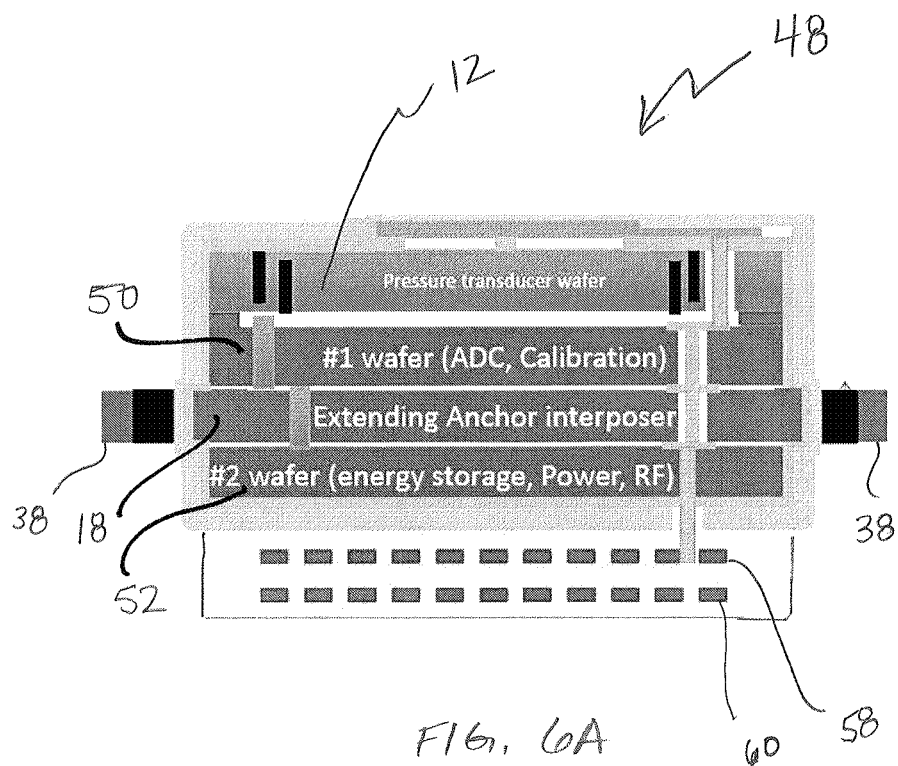
FIGS. 6A and 6B illustrate cross sectional front views of a vertically stacked implantable device according to embodiments of the invention.
Figure 6B:
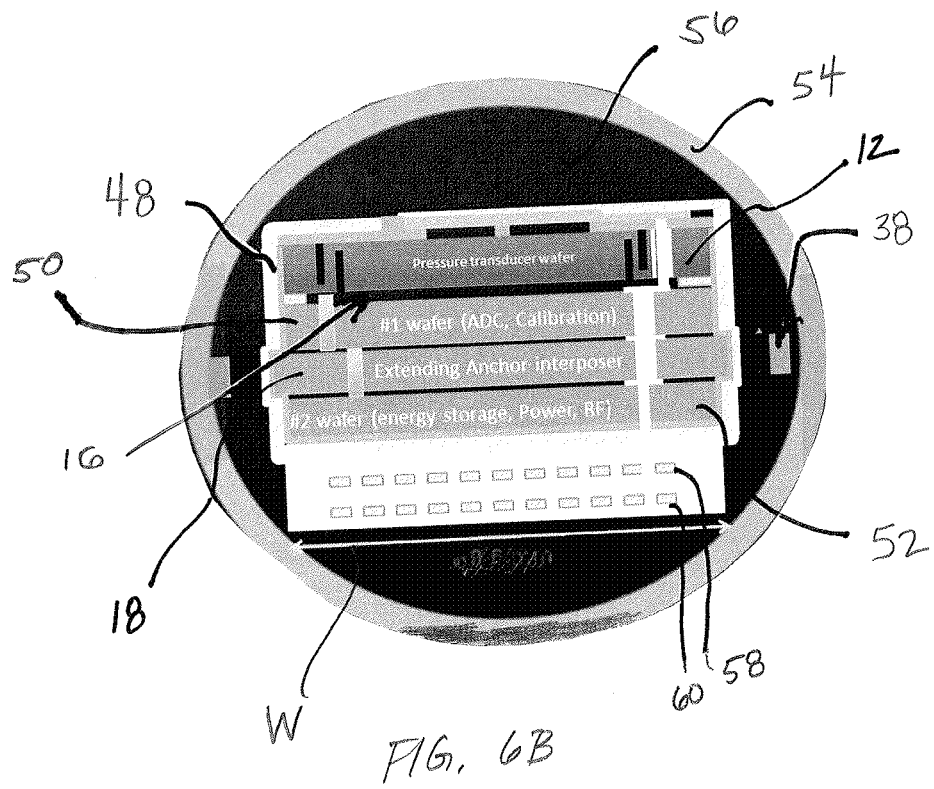

FIGS. 6A and 6B illustrate cross sectional front views of a vertically stacked implantable device 48 according to embodiments of the present invention. FIG. 6A illustrates the pressure transducer wafer 12 over a dual ASIC stack 50, 52 as another option to provide a smaller implant footprint depending on desired location and/or anchoring of implant.

The first ASIC wafer 50 may comprises components such as ADC, calibration, and data acquisition and logging. The second ASIC 52 may comprises a radio frequency link, power storage, and/or data storage. The anchoring interposer 18 may be disposed between the first and second ASIC wafers 50, 52. The implantable device 48 further comprises two vertically stacked coils 58, 60 disposed under the second ASIC 52 or an interdigitated double-coil, such as that shown in FIG. 4D. While the illustrated coil is shown with a glass substrate, typically a high aspect ratio dielectric polymer (polyimide, parylene, etc.) is used to form the coil shape around a gold conductor, although it is appreciated that the coil(s) may be formed using various other materials and according to other configurations. In certain embodiments utilizing a double coil, the first coil 58 may be utilized for power receipt while the second coil 60 may be configured for data transmission. In one aspect, a larger inductive coil may be attached if desired to increase the antenna side for improved coupling so as to allow for higher energy harvesting. Such a coil could be attached on the backside of the device or included at various different locations on the sensor device so long as its placement would not interfere with pressure measurements by the sensing capacitor.

FIG. 6B illustrates the implantable device 48 within a fluid-filled delivery syringe 54 for implantation by injection into the eye. In some embodiments, the implantable device 48 is sized so that it is capable of implantation through the inner diameter of the injector or syringe 54 having a gauge of 19 or higher. Preferably, the syringe 54 will be filled with biocompatible fluids 56, such as saline and the like, which helps protect the fragile pressure sensor membrane 22 of the MEMS wafer 12 from any inadvertent damage during implantation and further aids in positioning the implantable device 48 at the desired implantation site within the eye.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A vertically stacked and hermetically sealed implantable pressure sensor device for measuring a physiological signal, the implantable device comprising:
   a first wafer comprising at least a pressure sensor defined within the first wafer, the pressure sensor being configured to measure the physiological signal; and
   a second wafer comprising at least a digitizing integrated circuit defined within the second wafer,
   wherein the first wafer is vertically stacked with the second wafer so as to form a hermetic seal;
   wherein the entire implantable device is configured for implantation through an injector or syringe,
   wherein the first and second wafers are electrically connected by vertical connections by through wafer via (TWV),
   wherein the entire implantable device is of a size and shape capable of implantation through the injector or syringe of a gauge of 19 or higher, and wherein the pressure sensor comprises a first cavity structure and a second cavity structure defined within the first wafer, the first cavity structure configured for obtaining a pressure measurement signal and the second cavity structure being configured for obtaining a reference signal for comparison with the pressure measurement signal, wherein the first and second cavity structures are defined within the first wafer at laterally offset in-plane locations within the first wafer to facilitate the entire implantable device for implantation through the injector or syringe of a gauge of 19 or higher.

2. The implantable device of claim 1, wherein the vertical stacking of the wafers is configured to create a hermetically sealed cavity between the first and second wafers, wherein the hermetically sealed cavity comprises at least the first cavity.

3. The implantable device of claim 1, wherein the physiological signal comprises an intraocular pressure, an intracranial pressure, or a cardiovascular pressure.

4. The implantable device of claim 3, wherein the implantable device is sized or shaped to be positionable within a vitreous body of an eye so as to measure the intraocular pressure of a vitreous humour.

5. The implantable device of claim 1, wherein the pressure sensor comprises a capacitive pressure transducer.

6. The implantable device of claim 5, wherein the capacitive pressure transducer comprises at least the first cavity structure having a first membrane portion, wherein the first cavity structure k under vacuum such that the physiological signal comprises the pressure measurement signal.

7. The implantable device of claim 1, wherein the second wafer further comprises any of radio frequency link, power storage, and data storage.

8. The implantable device of claim 1, wherein each wafer comprises a maximum thickness of 200 microns or less.

9. The implantable device of claim 1, wherein each wafer has the same thickness.

10. The implantable device of claim 1, wherein the first wafer has a greater thickness than the second wafer.

11. The implantable device of claim 1, wherein the implantable device comprises a maximum thickness of 200 microns or less, a maximum length of about 4 mm or less, and a width of 650 microns or less.

12. The implantable device of claim 1, wherein the first and second wafers are formed from substrate materials having matched temperature coefficients of expansion or wherein the first and second wafers comprise the same material.

13. The implantable device of claim 1, further comprising at least one stress isolation feature incorporated into the first wafer to mechanically decouple the pressure sensor from the second wafer.

14. The implantable device of claim 1, further comprising a sealing ring disposed between the first and second wafers configured to hermetically seal the first and second wafers.

15. The implantable device of claim 14, further comprising a dielectric layer disposed over the implantable device to electrically isolate and encapsulate the first and second wafer and provide an adhesion layer.

16. The implantable device of claim 15, further comprising a titanium barrier disposed over the dielectric layer so as to further hermetically encapsulate the first and second wafers.

17. The implantable device of claim 16, further comprising a biocompatible polymer coating disposed over the titanium barrier.

18. The implantable device of claim 1, wherein all electrical connections are located on a bottom or back side of the first and second wafers so as to provide an interface to a media which is isolated from any electrical connection.

19. The implantable device of claim 1, further comprising a third wafer having a capacitor configured for providing power to the implantable device, wherein the second wafer is vertically stacked with the third wafer.

20. The implantable device of claim 19, further comprising a fourth wafer having a thin-film battery, wherein the third wafer is vertically stacked with the fourth wafer.

21. A vertically stacked and hermetically sealed implantable pressure sensor device for measuring a physiological signal, the implantable device comprising:
   a first wafer comprising at least a pressure sensor defined within the first wafer, the pressure sensor being configured to measure the physiological signal; and
   a second wafer comprising at least a digitizing integrated circuit defined within the second wafer,
   wherein the first wafer is vertically stacked with the second wafer so as to form a hermetic seal;
   wherein the entire implantable device is configured for implantation through an injector or syringe,
   wherein the first and second wafers are electrically connected by vertical connections by through wafer via (TWV),
   wherein the entire implantable device is of a size and shape capable of implantation through the injector or syringe of a gauge of 19 or higher,
   wherein the pressure sensor comprises a capacitive pressure transducer, wherein the capacitive pressure transducer comprises at least a first cavity structure having a first membrane portion, wherein the first cavity structure is under vacuum such that the physiological signal comprises a pressure measurement,
   wherein the capacitive pressure transducer Further comprises at least a second cavity structure having a second membrane portion, wherein the second cavity structure is under vacuum and the second membrane portion has a reduced area as compared to the first membrane portion such that the second membrane portion has a stiffness higher than the first membrane portion of the first cavity structure so as to be less sensitive to pressure such that a signal obtained from the second cavity comprises a reference measurement for comparison with the pressure measurement.

22. A vertically stacked implantable device for directly measuring an intraocular pressure of an eye of a patient, the implantable device comprising:
   a first wafer comprising at least a pressure transducer defined therein that is configured to directly measure the intraocular pressure of the eye; and
   a second wafer comprising at least a digitizing integrated circuit defined therein, wherein the first wafer is vertically stacked with the second wafer;
   wherein the implantable device is sized or shaped to be positionable within a vitreous body of the eye so as to measure the intraocular pressure of a vitreous humour of the vitreous body,
   wherein the first and second wafers are electrically connected by vertical connections by through silicon via (TSV) such that the device is sufficiently small to be injected through a syringe,
   wherein the pressure sensor comprises a first cavity structure and a second cavity structure defined within the first wafer, the first cavity structure configured for obtaining a pressure measurement signal and the second cavity structure being configured for obtaining a reference signal for comparison with the pressure measurement signal, wherein the first and second cavity structures are defined within the first wafer at laterally offset in-plane locations within the first wafer to facilitate the entire implantable device for implantation through the syringe.

23. The implantable device of claim 22, wherein the vertical stacking of the wafers is configured to create a hermetically sealed cavity between the first and second wafers, wherein the hermetically sealed cavity comprises at least the first cavity structure.

24. The implantable device of claim 22, wherein the pressure transducer comprises the first and second cavity structures, wherein the first cavity structure is distal of the second cavity structure along an implantation direction and configured to measure the intraocular pressure while the second cavity structure is configured to measure the reference signal.

25. The implantable device of claim 24, further comprising at least one coil vertically stacked or disposed over the first wafer and the second cavity structure while the first cavity structure remains exposed.

26. The implantable device of claim 22, wherein the second wafer further comprises any of a radio frequency link, power storage, and data storage.

27. The implantable device of claim 22, further comprising a third wafer having a capacitor configured for providing power to the implantable device, and a fourth wafer having a thin film battery vertically stacked with the first and second wafers, wherein the third wafer is disposed between the second and fourth wafers.

28. The implantable device of claim 22, further comprising an interposer disposed below the second wafer, wherein the interposer comprises an anchoring means, a distal tissue-penetrating tip, or an extraction feature.

29. The implantable device of claim 28, wherein the interposer further comprises at least one capacitor for supplemental energy storage or least one coil configured to receive power or transmit data.

30. The implantable device of claim 22, wherein the pressure transducer has a full scale range from −100 mmHg to 200 mmHg around 1 Atmosphere with a pressure resolution of 0.5 mmHg and full range sensitivity in the order of magnitude of 1 pF or 20% of the transducer capacitance.

31. An injectable intraocular pressure sensor system, the system comprising:
 a fluid-filled syringe or injector; and
 an implantable intraocular pressure sensor device comprising:
 a first wafer comprising at least a pressure sensor configured to measure a physiological signal; and
 a second wafer comprising at least a digitizing integrated circuit, wherein the first wafer is vertically stacked with the second wafer,
 wherein the first and second wafers are electrically connected by vertical connections by through wafer via (TWV),
 wherein the entire implantable intraocular pressure sensor device is of a size and shape for implantation through the fluid-filled injector or syringe into an eye,
 wherein the pressure sensor comprises a first cavity structure and a second cavity structure defined within the first wafer, the first cavity structure configured for obtaining a pressure measurement signal and the second cavity structure being configured for obtaining a reference signal for comparison with the pressure measurement signal, wherein the first and second cavity structures are defined within the first wafer at laterally offset in-plane locations within the first wafer to facilitate the entire implantable intraocular pressure sensor device for implantation through the fluid-filled injector or syringe into the eye.

32. The system of claim 31, wherein the implantable intraocular pressure sensor device further comprises a third wafer having a capacitor configured for providing power to the implantable intraocular pressure sensor device, and a fourth wafer having a thin film battery vertically stacked with the first and second wafers, wherein the third wafer is disposed between the second and fourth wafers.

* * * * *

UNITED STATES PATENT AND TRADEMARK OFFICE
CERTIFICATE OF CORRECTION

PATENT NO. : 10,973,425 B2  
APPLICATION NO. : 14/789839  
DATED : April 13, 2021  
INVENTOR(S) : Ariel Cao Page 1 of 1

It is certified that error appears in the above-identified patent and that said Letters Patent is hereby corrected as shown below:

In the Claims

Column 13, Line 30, Claim 6: please delete "structure k under" and insert --structure is under--.

Signed and Sealed this  
Twenty-second Day of June, 2021

Drew Hirshfeld  
*Performing the Functions and Duties of the*  
*Under Secretary of Commerce for Intellectual Property and*  
*Director of the United States Patent and Trademark Office*